United States Patent
Gabriel

(10) Patent No.: US 9,404,933 B2
(45) Date of Patent: Aug. 2, 2016

(54) METHODS FOR DETERMINING PATIENT RESPONSE TO ANTI-PLATELET AGGREGATION THERAPY

(75) Inventor: Don Gabriel, Carrboro, NC (US)

(73) Assignee: INVITROX, INC., Durham, NC (US)

( * ) Notice: Subject to any disclaimer, the term of this patent is extended or adjusted under 35 U.S.C. 154(b) by 18 days.

(21) Appl. No.: 14/233,876

(22) PCT Filed: Jul. 20, 2012

(86) PCT No.: PCT/US2012/047763
§ 371 (c)(1),
(2), (4) Date: Mar. 31, 2014

(87) PCT Pub. No.: WO2013/013228
PCT Pub. Date: Jan. 24, 2013

(65) Prior Publication Data
US 2014/0200240 A1      Jul. 17, 2014

Related U.S. Application Data

(60) Provisional application No. 61/510,442, filed on Jul. 21, 2011.

(51) Int. Cl.
| | | |
|---|---|---|
| *A61K 31/44* | (2006.01) | |
| *G01N 33/567* | (2006.01) | |
| *G01N 33/86* | (2006.01) | |
| *G01N 33/49* | (2006.01) | |
| *A61K 31/4365* | (2006.01) | |
| *G01N 15/00* | (2006.01) | |
| *G01N 15/14* | (2006.01) | |

(52) U.S. Cl.
CPC ............ *G01N 33/86* (2013.01); *A61K 31/4365* (2013.01); *G01N 33/49* (2013.01); *G01N 15/1459* (2013.01); *G01N 2015/0053* (2013.01); *G01N 2015/1493* (2013.01)

(58) Field of Classification Search
CPC .................. G01N 2015/1493; G01N 15/1459; G01N 2015/0053; G01N 2015/0084; G01N 2015/1486; G01N 33/49; G01N 33/86; A61K 31/4365
USPC ............. 435/7.21, 7.24, 7.25, 287.1; 514/301
See application file for complete search history.

(56) References Cited

U.S. PATENT DOCUMENTS

| | | | | |
|---|---|---|---|---|
| 7,790,362 B2* | 9/2010 | Coller | ................... | G01N 33/86 435/4 |
| 8,455,207 B2* | 6/2013 | Gabriel | ................... | C12Q 1/04 435/7.2 |
| 8,551,405 B2* | 10/2013 | Gabriel | ................... | C12Q 1/04 422/82.05 |
| 8,551,406 B2* | 10/2013 | Gabriel | ................... | C12Q 1/04 422/82.05 |
| 8,735,056 B2* | 5/2014 | Toumbas | ............. | G01N 21/532 422/82.05 |
| 8,828,737 B2* | 9/2014 | Gabriel | ................ | G01N 15/147 435/7.21 |
| 2010/0190148 A1 | 7/2010 | Gabriel | | |
| 2014/0234865 A1* | 8/2014 | Gabriel | .............. | G01N 15/1459 435/7.21 |
| 2014/0377741 A1* | 12/2014 | Gabriel | ................ | G01N 15/147 435/5 |

FOREIGN PATENT DOCUMENTS

WO        2004010113 A1      1/2004

OTHER PUBLICATIONS

Gratsianskiy, N.A., Antitrombombotsitarnaya terapiya pri koronamoy bolezni serdtsa. Nekotorye problemy i dostizheniya., Aterotromboz, 2010, No. 1(4).
Althoff, E., "Novartis gains worldwide rights to elinogrel, a Phase II anti-clotting compound with potential to reduce reisk of heart attack and stroke", Novartis Media Relations, Feb. 12, 2009.
International Search Report for corresponding PCT Application No. PCT/US2012/047763 dated Nov. 1, 2012.
International Preliminary Report on Patentability for corresponding PCT Application No. PCT/US2012/047763 dated Jan. 30, 2014.

\* cited by examiner

*Primary Examiner* — My-Chau T Tran
(74) *Attorney, Agent, or Firm* — Andrews Kurth LLP; David Bradin

(57) ABSTRACT

Diagnostic methods for determining whether an individual will benefit from a particular anti-thrombotic therapeutic agent are disclosed. The methods involve obtaining a biological sample that comprises platelets, from a patient who has been pre-administered a particular therapeutic agent, which is an antagonist of a receptor associated with the biochemical pathways involved in platelet aggregation, and exposing the platelets to an agonist of the receptor. If the antagonist is ineffective, the platelets will eject microparticles, will have a different size distribution than platelets not exposed to the agonist, and will experience a change in their surface charge. In one embodiment, the diagnostic methods involve using single particle optical sizing techniques to determine the presence of such ejected microparticles, or a change in platelet size due to its activation by the agonist. In another embodiment, electrophoretic quasi-elastic light scattering techniques are used to determine the presence of a change in surface charge on the platelets. Once an effective therapeutic agent, or an effective dosage of such therapeutic agent, has been identified, the patient can begin therapy knowing that the agent will be effective.

19 Claims, 14 Drawing Sheets

METHODS FOR DETERMINING PATIENT RESPONSE TO ANTI-PLATELET AGGREGATION THERAPY

CROSS-REFERENCE TO RELATED APPLICATIONS

This application is a U.S. national phase under the provisions of 35 U.S.C. §371 of International Patent Application No. PCT/US12/47763 filed Jul. 20, 2012, which in turn claims priority of U.S. Provisional Patent Application No. 61/510,442 filed Jul. 21, 2011. The disclosures of such international patent application and U.S. priority provisional patent application are hereby incorporated herein by reference in their respective entireties, for all purposes.

FIELD OF THE INVENTION

This application is generally in the area of the use of single particle optical light scattering techniques and/or electrophoretic quasi-elastic light scattering techniques to determine whether a patient will or will not respond to P2Y12 antagonists, such as clopidogrel bisulfate (Plavix®). The application is also related to the use of these techniques to determine whether a patient will response to other anti-thrombotic agents that inhibit other platelet activation receptors, such as PAR1, PAR4, GPIV, TP-alpha, TP-beta, and GPIIb/IIIa antagonists.

BACKGROUND OF THE INVENTION

Platelet activation and aggregation underlies the basic "acute event" in arterial thrombosis, including strokes, peripheral artery disease and coronary artery disease (heart attacks). In the field of molecular biology, the P2Y12 protein is found on the surface of blood platelet cells, and is an important regulator in blood clotting (Dorsam and Kunapuli, "Central role of the P2Y12 receptor in platelet activation," J. Clin. Invest. 113 (3): 340-5 (2004)), which can lead to arterial thrombosis. P2Y12 belongs to a group of G protein-coupled purinergic receptors (Murugappa and Kunapuli, "The role of ADP receptors in platelet function," Front. Biosci. 11: 1977-86 (2006)) and is a chemoreceptor for adenosine diphosphate (ADP) (Hollopeter et al., "Identification of the platelet ADP receptor targeted by antithrombotic drugs," Nature 409 (6817): 202-7 (2001)), (Nicholas, "Identification of the P2Y (12) receptor: a novel member of the P2Y family of receptors activated by extracellular nucleotides". Mol. Pharmacol. 60 (3): 416-20 (2001)). The P2Y family has several receptor subtypes with different pharmacological selectivity, which overlaps in some cases, for various adenosine and uridine nucleotides. This receptor is involved in platelet aggregation, and is a potential target for the treatment of thromboembolisms and other clotting disorders.

Adenosine-5'-diphosphate (ADP) plays a key role in platelet function, because, although ADP itself is a weak platelet agonist, when secreted from the platelet dense granules where it is stored, it amplifies the platelet responses induced by other platelet agonists. The transduction of the ADP signal involves both a transient rise in free cytoplasmic calcium mediated by the Gq-coupled P2Y1 receptor, and inhibition of adenylyl cyclase mediated by the Gi-coupled P2Y12 receptor. Concomitant activation of both the Gq and Gi pathways by ADP is necessary to elicit normal ADP-induced platelet aggregation. Activation of the Gq pathway through P2Y1 leads to platelet shape change and rapidly reversible aggregation, whereas the activation of the G1 pathway through P2Y12 elicits a slow progressive and sustained platelet aggregation not preceded by shape change. In addition to its role in ADP-induced platelet aggregation, P2Y12 mediates the potentiation of platelet secretion induced by strong agonists and the stabilization of thrombin-induced platelet aggregates. P2Y12 has a more selective tissue distribution than P2Y1, making it an attractive molecular target for therapeutic intervention.

Current drug therapy involves using irreversible P2Y12 antagonists to bind to the surface P2Y12 receptors, so that the platelets to not bind to P2Y12 agonists such as adenosine diphosphate (ADP). Platelets not bound to one of these antagonists, whether reversibly or irreversibly, will bind to ADP.

The drug clopidogrel (Plavix®) is a P2Y12 antagonist that binds to the P2Y12 receptor on the platelet surface, and is marketed as an anti-thrombotic agent. When the active part of the drug is bound to P2Y12, the usual P2Y12 agonist ADP cannot bind. When ADP is blocked from its P2Y12 binding site, platelet activation is inhibited. In responding patients, this drug is life-saving. Unfortunately, Plavix® is ineffective in about 30% of the population. The major cause of resistance is failure to activate the drug in the liver. Patients who have CYT2C19, and possibly other cytochrome alleles, do not activate Plavix. In addition, there is polymorphism in P2Y12, found on the surface of platelets in some patients, which may also cause resistance. For this reason, some patients who have the ability to produce the active metabolite are still unable to benefit from Plavix®, due to an abnormality in their platelets.

Further, there is a delay to the anti-platelet aggregating effects, due to the fact that Plavix®) must be metabolized to form the active agent. A maximum plateau of inhibition of ADP-induced platelet aggregation is observed 4-5 days after daily oral administration of 75 mg Plavix® (or 500 mg ticlopidine). However, the delayed onset of action of Plavix® can be reduced to about two to five hours with a loading dose of 300-600 mg.

Prasugrel® (Eli Lilly) is a relatively new entrant to this market. Next generation P2Y12 receptor antagonists include ticagrelor and elinogrel. Ticlopidine and clopidogrel are structurally related compounds, belonging to the thienopyridine family of ADP receptor antagonists. They are pro-drugs that are inactive in vitro, and need to be metabolized in vivo by the hepatic cytochrome P-450 1A enzymatic pathway to active metabolites, which have very short half-lives. The active metabolites irreversibly and
specifically inhibit the function of the platelet P2Y12 receptor, reproducing the platelet function abnormalities that are observed in patients who are congenitally deficient in P2Y12 and in P2Y12 knock-out mice.

There is a substantial inter-individual variability in platelet inhibition by ticlopidine and clopidogrel, mostly due to the inter-individual differences to the extent of metabolism of the pro-drug to the active metabolite. Certain individuals taking clopridogrel can have insufficient inhibition of platelet function, with a concomitant higher incidence of vascular events, though some patients can achieve a beneficial effect by increasing the dose of clopidogrel. That said, those patients who take higher doses are at risk for severe toxic effects, such as bone marrow aplasia and microangiopathic thrombocytopenia, which are thought to be dose-dependent. These toxic side effects also occur, though less frequently, with ticlopidine. Because of these limitations, there has been significant research to develop new P2Y12 antagonists. Prasugrel (2-acetoxy-5-[alpha-cyclopropylcarbonyl-2-fluorobenzyl]-4,5,6, 7-tetrahydrothieno[3,2-c]pyridine), a relatively new thienopyridine compound, has a much faster onset of action than clopidogrel. Prasugrel is structurally similar to other thienopyridines. The active metabolite of Prasugrel (R-138727), a sulfhydryl compound, binds covalently and irreversibly to the platelet P2Y12 receptor via a disulfide bond. As with clopridogrel, the irreversible binding of the active metabolite permanently blocks ADP-mediated P2Y12 signaling, and inhibits both glycoprotein IIb/IIIa receptor activation and platelet aggregation.

In a cross-over study, a 60 mg loading dose of Prasugrel provided rapid and highgrade, irreversible inhibition of ADP-induced platelet aggregation even in those subjects who responded poorly to a standard loading dose of Clopidogrel. The higher potency of Prasugrel compared with Clopidogrel probably reflects more efficient conversion of the pro-drug to the active metabolite. Prasugrel (marketed by Eli Lilly in the U.S. as Effient®) has proven safe and effective, but is currently only approved for use in angioplasty patients, and is associated with an increased risk of fatal bleeding. Accordingly, patients who can benefit from Plavix® may still wish to take Plavix®, even though there is another P2Y12 antagonist on the market.

Because these agents irreversibly inhibit P2Y12 function, the inhibitory effect of thienopyridines on circulating platelets lasts for approximately 10 days (the lifespan of a circulating platelet). While this is an advantage for patients, it can represent a problem for patients who need to undergo coronary bypass surgery, because treatment with clopidogrel within 4-5 days of the procedure is associated with increased blood loss, reoperation for bleeding, increased transfusion requirements, and prolonged intensive care unit and hospital length of stay. For this reason, there has been significant research to identify anti-thrombotic agents that reversibly inhibit P2Y12 function.

In some clinical situations, inhibition of platelet aggregation by fast-acting and reversible antagonists with a short half-life might be preferable to irreversible inhibitors. Cangrelor is a selective and reversible direct inhibitor of P2Y12. In a study that directly compared the effects of clopidogrel and cangrelor administration in patients with ischaemic heart disease, cangrelor infusion at 2 and 4 µg/mL/min resulted in near complete inhibition of platelet aggregation measured at 4 min after the addition of 10 µM ADP, whereas 4 to 7 days clopidogrel treatment resulted in only approximately 60% inhibition. The short half-life of the molecule (2.6 min) results in a rapid reversal of its platelet inhibitory effect. Addition of cangrelor in vitro to blood from the clopidogrel treated patients resulted in near complete inhibition of P2Y12-dependent platelet function. It must be noted, however, that cangrelor can only be given intravenuously, which limits its use in the clinical practice, and it did not show sufficient benefit to patients in a Phase III clinical trial to warrant FDA approval.

Brilinta (Ticagrelor, marketed by Astra Zeneca) is an orally administrable, reversible P2Y12 antagonist. Brilinta belongs to the same family as cangrelor of stable ATP analogues with high affinity for P2Y12. Brilinta is currently approved for sale in Europe, though at the time of this filing was not approved for sale in the United States.

Clopidogrel was issued a black box warning from the FDA on Mar. 12, 2010, as the estimated 2-14% of the US population that have low levels of the CYP2C19 liver enzyme needed to activate clopidogrel may not get the full effect. As metabolism of Prasugrel has not been shown to be effected by the same CYP450 mutations, it remains a potentially viable agent for those who cannot benefit from Clopidogrel due to the presence of the CYP450 mutations. However, while the hypothesis that Prasugrel will work better in patients who cannot metabolize clopidogrel is appealing, it has not been verified in prospective clinical trials.

Now that alternatives to Plavix® have been approved, and generic clopidogrel bisulfate (i.e., generic equivalents of Plavix®) will be available in the near future, patients will be faced with a difficult choice—take generic, relatively low cost clopidogrel bisulfate with the concomitant risk that they will not benefit from such therapy, or take non-generic next-generation anti-thrombotic agents, and pay the higher price for the non-generic therapy. Further, if a patient takes a drug that provides little or no benefit, the patient is at an elevated risk of a severe cardiovascular event, such as a myocardial infarction.

Thus, while physicians have more than one P2Y12 inhibitor (antagonist) to choose from, it would be useful for them to have the ability to tailor the most appropriate anti-thrombotic therapy to the individual patient and risk situation. Because not every patient can benefit from every P2Y12 inhibitor, it would be useful to have a rapid and inexpensive assay to determine whether or not a patient is able to respond to Plavix® other anti-thrombotic agents.

In terms of developing an appropriate assay, there is a correlation between patients who have mutations in the Cytochrome P-450 gene, specifically, in CYT2C19, and possibly other cytochrome alleles, do not activate Plavix®, and may not benefit from clopidogrel. However, even if the assay identifies a patient as one who can metabolize Plavix®, there is polymorphism in P2Y12 that may also cause resistance, and patients who have this mutation would not be identified unless the pharmacogenomic screening also looked for these mutations.

In any event, pharmacogenomic screening assays are available to predict whether or not a patient is susceptible to this problem. However, pharmacogenomic screening is relatively expensive, and it takes a significant amount of time to obtain the results. Because the use of pharmacogenomic assays is not widespread, patients have been prescribed Plavix® who may derive no benefit from it. As a result, patients have been faced with relatively high costs, and potentially relatively little or no efficacy. From an economic perspective, roughly 30% of patients are deriving little or no benefit form Plavix®, so in the US approximately $1.6 billion/year is spent on a drug that is not appropriate for the patients. This waste could be avoided by identifying those patients who are not expected to respond favorably to this agent, or to other anti-thrombotic agents. However, as it has been estimated that the cost of a 2C19 screen is around $500, and around 100 million patients have been prescribed Plavix, the cost of screening all of these patients would be around $50 billion. Further, unless one can identify patients with a polymorphism in P2Y12 that also renders platelets non-responsive to Prasugrel, Clopidogrel, or other P2Y12 antagonists, patients might also be administered these agents, and not benefit from them.

Accordingly, a less expensive assay is needed, as is an assay that will identify patients who are non-responsive because of mutations in their CYP450 genes, or mutations in their P2Y12 receptor. Genetic screening to identify patients with the CYP 2C19*2 and *3 alleles will identify most, but not all of the patients who cannot activate the prodrug. Screening of platelets from patients taking the drug to show whether their platelets activate after exposure to the appropriate agonist is the only way to identify for certain all resistant patients.

Currently there is no effective assay to screen patients to determine with certainty whether their platelets will bind to P2Y12 antagonists, that is, whether the patient can actually metabolize the drug, and whether the active metabolite is capable of binding to the patient's platelets. If resistant patients (whether resistance is due to genetic variations in pro-drug metabolism or in the shape of the platelet P2Y12 receptor shape) could be effectively identified, it may be possible to increase the dose of Plavix in these patients and thus salvage them with a higher dose that could prove effective therapy. In addition to P2Y12, there are other receptors involved in thrombosis and platelet aggregation. These include Protease-Activated Receptor 1 (PAR1), Protease-Activated Receptor 4 (PAR4), GPIV, Thromboxane receptor (TP receptor, including TP-alpha and TP-beta), vWF antagonists, and Glycoprotein Ib (platelet), alpha polypeptide (GP1BA) also known as CD42b (Cluster of Differentiation 42b), GPIb, antagonists, and Glycoprotein (GPIIb/IIIa) antagonists.

As there would be clear benefits associated with being able to determine whether or not a patient would benefit from taking one of these anti-thrombotic agents, it would be useful to have a rapid and inexpensive assay to determine whether or not a patient will respond to a particular anti-platelet aggregation therapy. The present invention provides such an assay.

SUMMARY OF THE INVENTION

Diagnostic methods for screening patients for their ability to benefit from antithrombotic therapy are disclosed. Theranostic methods, wherein a patient is screened according to the diagnostic methods described herein, and then treated with a particular anti-thrombotic agent, are also disclosed.

In one embodiment, the diagnostic method involves looking for the presence or absence of microparticles that are ejected or shed from platelets following exposure to a P2Y12 agonist. Platelets whose surface receptors are bound with a P2Y12 antagonist, reversibly or irreversibly, will not bind to the P2Y12 agonist, and, accordingly, will not eject microparticles. As a biological sample comprising platelets will typically include microparticles even in the absence of binding an agonist to the cell surface receptors, it can be beneficial to determine the number of microparticles in the sample both before and after exposure to the agonist. An increase in the number of microparticles in the sample, following exposure to a P2Y12 agonist, is indicative of the platelet not being bound to a P2Y12 antagonist. If there is no significant increase in the number of microparticles in the sample following exposure to a P2Y12 agonist, it is indicative that the platelet is bound to a P2Y12 antagonist. Representative P2Y12 antagonists that can be screened include Ticlopidine, Clopidogrel, Parasurgrel, Elinogrel, Cangrelor, Ticangrelor, BX667, and PRT 060128.

Where the anti-thrombotic agent is a prodrug (such as Plavix® or Prasugrel®), the method involves first obtaining a biological sample comprising platelets from a patient who has been pre-dosed with the anti-thrombotic agent for which a determination of efficacy is desired. The dosing can either be a loading dose, or can be a dose given over a certain time period known, for each drug, to provide a predetermined plasma concentration of the drug. Where the anti-thrombotic agent is not a prodrug, a suitable amount (which will vary depending on the number of platelets in the sample) of anti-thrombotic agent is added to the biological sample. In either case, the sample can be a raw blood sample, or, for example, can be a sample resulting from the centrifugation of a blood sample and the isolation of a platelet-rich fraction thereof.

Because the microparticles (MPs) are relatively small, on the order of 0.1 to 1.0 µn, the sample is passed through an instrument that can detect the presence of particles in this size range. One example of such a device is described, for example, in PCT WO/2010/017001 by Invitrox, entitled "Use of Focused Light Scattering Techniques in Biological Applications." The use of a focused laser beam in a single particle optical sizing device, among other features, allows one to measure smaller particle sizes than can otherwise be measured when the light source is not focused, such as in a Coulter counter.

In another embodiment, the diagnostic method involves using EQELS or other methods for determining particle mobility through an electric field to determine whether receptors on the surface of the platelets in the patient sample have bound to the antithrombotic agent. This embodiment takes advantage of the change in surface charge on a normal platelet (i.e., a negative charge) once it is activated with an agonist (i.e., a positive charge). When passed through an electric field following exposure to an agonist, the platelets will either move towards or away from a positive (or negative) charge in the electrophoretic quasi-elastic light scattering (EQELS) device. Positively charged platelets are indicative of the inability of a patient to benefit from the particular antithrombotic agent, and negatively charged platelets are indicative of the ability of a patient to benefit from the particular antithrombotic agent (or a particular dosage of the agent). The electrophoretic method is dependent on the suspended platelets surface charge density that provides an electrostatic finger print for the cell in it current metabolic state. EQELS places the platelets in an electric field, and the surface charge of the platelet determines how that particle moves in the electric field. Monitoring the electrophoretic mobility of the platelets, following exposure to an agonist such as ADP, allows one to quickly and easily determine whether a patient will benefit from a particular antithrombotic agent, or from different concentrations of that agent. One can screen patients for their ability to benefit from a particular anti-thrombotic agent, and/or a particular dose of the agent, using this approach.

Using either of these diagnostic approaches, a physician can then identify an appropriate anti-thrombotic agent, and dosage, and administer them to the patient. In addition to the P2Y12 receptor, a number of other receptors are involved in platelet aggregation. Other anti-thrombotic agents include antagonists (inhibitors) of receptors such as Protease-Activated Receptor 1 (PAR1), Protease-Activated Receptor 4 (PAR4), glycoprotein IV (GPIV), Thromboxane receptor (TP receptor, including TPalpha and TP-beta), vWF antagonists, and Glycoprotein Ib (platelet), alpha polypeptide (GP1BA) also known as CD42b (Cluster of Differentiation 42b), GPIb, antagonists, and Glycoprotein (GPIIb/IIIa) antagonists. Terutroban is a representative TP inhibitor. Representative PAR1 inhibitors include SCH 530348, SCH 205831, SCH 602539, and E5555. Representative GP1b inhibitors include vWF, ARC 1779, ALX 0081 and AJW 200. Representative GPIIb/IIIa inhibitors include Rheopro, Abciximab, Eptifibatide, and Tirofiban. In another embodiment of the invention, these inhibitors are also screened using methods analogous to those described above with respect to P2Y12.

Whereas the embodiments related to P2Y12 antagonists involve incubating cells with a P2Y12 antagonist, and exposing the incubated cells to a P2Y12 agonist, these embodiments involve incubating the cells with a PAR1, PAR4, GPIV, TP receptor (including TP-alpha and TP-beta), GPIb, or GP1BA antagonist, or GPIIb/IIIa agonist. For purposes of consistency, although GPIIb/IIIa agonists (not antagonists) are used to inhibit the action of antagonists (not agonists), which antagonists promote platelet aggregation, the application will refer to the GPIIb/IIIa agonists as antagonists, and the GPIIb/IIIa antagonists as agonists, where agonism is understood to refer to a biological action that promotes platelet aggregation, and antagonism is understood to refer to inhibition of the action of the agonist that promotes platelet aggregation. The incubated cells are then exposed to the corresponding agonists. For PAR1, thrombin is a suitable agonist. For GP-1b, von Willebrand Factor (vWF) is a suitable agonist. For TP receptors, thromboxane A2 (TXA2) is a suitable agonist. The peptide AYPGKF is a representative PAR-4 agonist, which is known to stimulate thromboxane production by human platelets (see, for example, Henrickson and Hanks, Arteriosclerosis, Thrombosis, and Vascular Biology. 2002; 22:861). EP80317 is a representative GPIV agonist.

The present invention will be better understood with reference to the following Detailed Description.

BRIEF DESCRIPTION OF THE DRAWINGS

FIG. 13 also shows the difference in the platelet surface. As shown in FIG. 13, un-activated platelets have a smooth surface structure, but when activated with an agonist, have a rougher surface structure.

DETAILED DESCRIPTION

Figure 1:
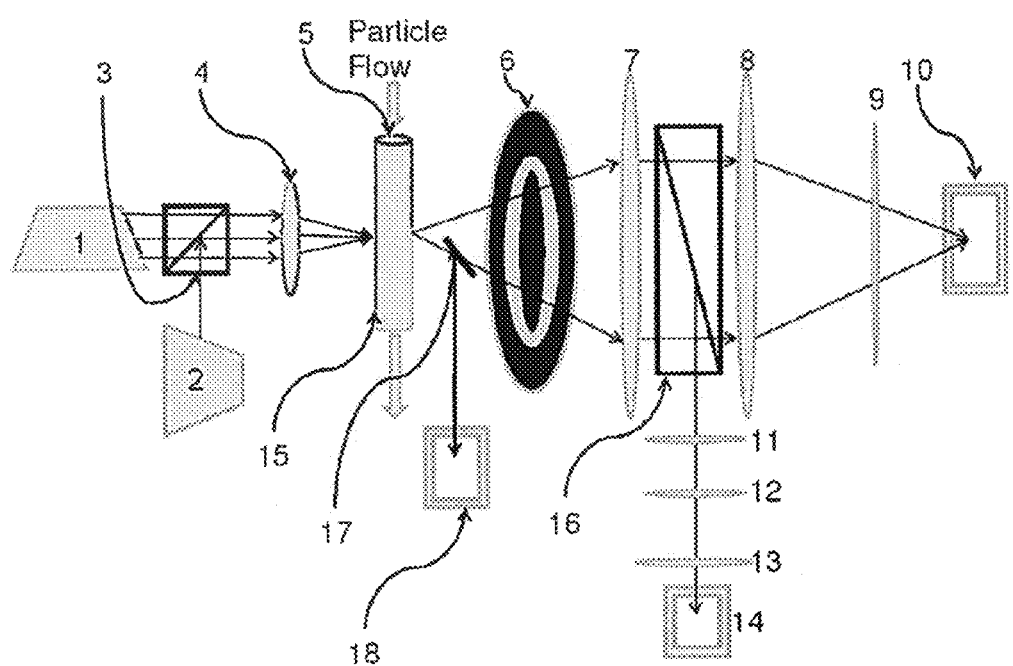
FIG. 1 is a schematic illustration of a single particle optical sizing device, referred to herein as a "surface antigen detection enumerator" light scattering device capable of measuring particles as small as around 0.01 μm in diameter.

Methods for screening patients to determine whether they will benefit from a particular anti-thrombotic therapy are disclosed. In one embodiment, the anti-thrombotic therapy involves the administration of a P2Y12 antagonist (inhibitor), and in other embodiments, the anti-thrombotic therapy involves the administration of one or more PAR1, PAR4, GPIV, TP (including TP-alpha and TP-beta), GPIb, GP1BA, or GPIIb/IIIa antagonists.

Theranostic methods, where the patient is first screened for his or her ability to benefit from a particular P2Y12, PAR1, PAR4, GPIV, TP (including TP-alpha and TP-beta), GPIb, GP1BA, or GPIIb/IIIa antagonist, or prodrug thereof, and is then treated with the P2Y12, PAR1, PAR4, GPIV, TP receptor (including TP-alpha and TP-beta), GPIb, GP1BA, or GPIIb/IIIa antagonist, or prodrug thereof, are also disclosed. Among other things, the assays of the present invention are useful for screening subjects, particularly human subjects or other mammalian subjects, for their ability to be treated with a putative P2Y12, PAR1, PAR4, GPIV, TP receptor (including TP-alpha and TP-beta), GPIb, GP1BA, or GPIIb/IIIa antagonist, or prodrug thereof, and thus subjected to lesser risk of stroke, myocardial infarction, and other disorders associated with thrombosis in an artery or vein.

The assays described herein can use any P2Y12, PAR1, PAR4, GPIV, TP receptor (including TP-alpha and TP-beta), GPIb, GP1BA, or GPIIb/IIIa agonist, as appropriate, following incubation of platelets with the corresponding P2Y12, PAR1, PAR4, GPIV, TP (including TP-alpha and TP-beta), GPIb, GP1BA, or GPIIb/IIIa antagonists, respectively.

ADP is a representative P2Y12 agonist. Terutroban is a representative TP inhibitor. Thrombin is a representative PAR1 and PAR2 inhibitor, and other PAR1 inhibitors include SCH 530348, SCH 205831, SCH 602539, and E5555. Representative GP1b inhibitors include vWF, ARC 1779, ALX 0081 and AJW 200. Representative GPIIb/IIIa inhibitors include Rheopro, Abciximab, Eptifibatide, and Tirofiban. In one embodiment, single particle optical sizing techniques are used to identify the presence of microparticles produced by activated platelets. Unbound platelets produce microparticles when activated with a P2Y12 agonist, such as ADP. Platelets are not activated by a P2Y12 agonist if they are bound to a P2Y12 antagonist, so no microparticles will be produced. Accordingly, the detection method involves measuring the number of microparticles in a patient's blood sample, or a fraction thereof that includes platelets and microparticles, then exposing the sample to a P2Y12 agonist. The number of microparticles in the sample is re-measured, and compared to the original number of microparticles. An increase in the number of microparticles indicates that the platelets were not bound to the antagonist, so the patient did not respond to the antiplatelet adhesion therapy.

Because the size of the microparticles is in the order of 0.1 micron, ordinary optical particle sizing techniques may not be suitable to carry out this assay. However, one can use an optical sizing apparatus that uses a focused beam of laser light, and, ideally, a focused sample passing through the beam of light. An example of a suitable single particle optical sizing apparatus is disclosed, for example, in U.S. application Ser. No. 12/502,941, the contents of which are hereby incorporated by reference. In the second embodiment, rather than measuring the microparticles that are ejected from the platelets if they are bound to a P2Y12 agonist, the electrophoretic mobility of the platelets is measured. Because the surface charge of the platelets changes from negative to positive upon exposure to a P2Y12 agonist, and subsequent platelet activation, the electrophoretic mobility of the particles is completely different depending on whether or not they are activated.

Figure 10:
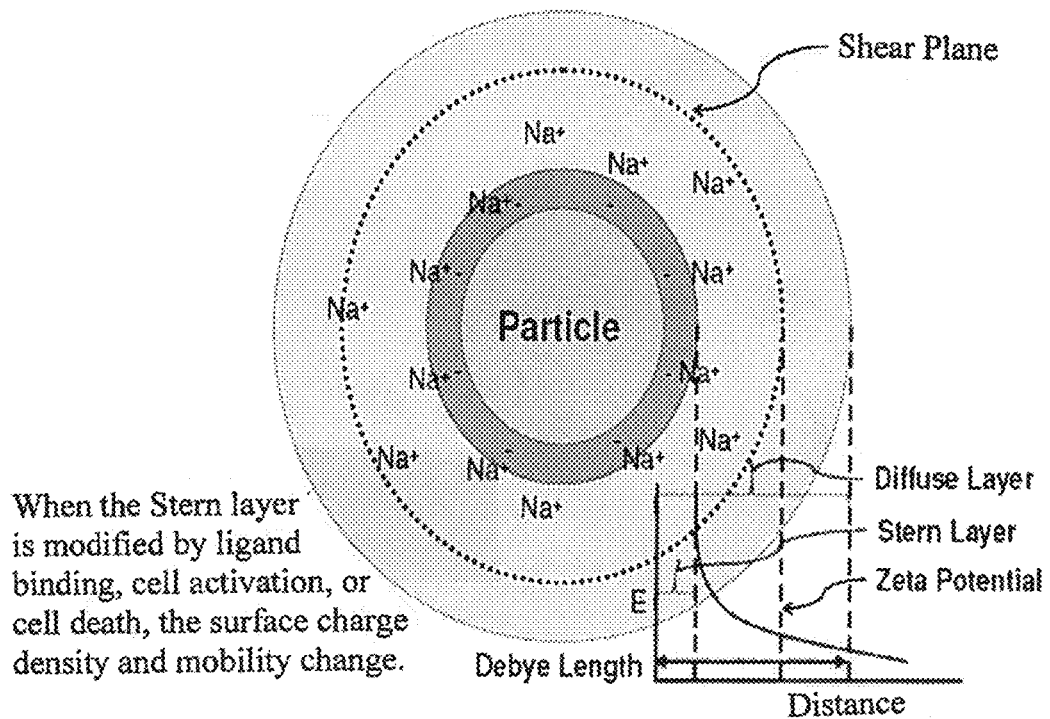
FIG. 10 is a schematic illustration showing the effect platelets on the cations in the solution that surrounds the particle as described by Debye Huckle theory. The yellow circle represents a platelet.

As shown in FIG. 10, a biological cell (such as a platelet) has an effect on the cations in the solution that surrounds the particles, as described by Debye Huckle theory. Platelets in the resting state have a negative surface charge. For a short distance out from the platelets, where the electrical potential is high, the positive ions in solution orient themselves around the cells. That layer is called the Stern layer. As one moves out farther the electric field, a decrease in strength as shown in the graph. In this area, the ordering of oppositely charged ions is not as distinct, and some negatively charged solution ions can enter this area. This layer is called the diffuse layer. The thickness of the diffuse layer is called the Debye length. EQELS works by making the cell move in an imposed electric field. Because the electric field at the far reaches of the diffuse plane is not intense enough to drag the entire cloud of ions with it, some are left behind. The distance from the cell surface where this occurs is called the "shear plane". The potential at that point is called the "zeta potential."

The surface charge density and mobility change when the Stern layer is modified by ligand binding, cell activation, or cell death. This change in mobility can be measured using electrophoretic quasi-elastic light scattering techniques (EQELS), as the particles are passed through an electric field.

The cell's surface charge density is an important feature of the cell. When the cell dies or activates or a drug or other molecule binds to the surface, the surface charge density changes. This can be thought of as a Surface Charge Finger Print (SCFP) or electrostatic finger print. This fingerprint can be used to detect very subtle changes in cells, in this case, in platelets. This important cell feature is exploited by using a very sensitive method to measure changes in how fast the cell moves in an electric field. This movement is referred to as the electrophoretic mobility (EM).

This is accomplished by using a Doppler method, similar to Doppler weather radar. It is relevant to note that is the method does not separate individual cells, but only measures the velocity at which each cell is moving in the electric field. This difference sets the method apart from other electrophoretic methods. The cells are not separated, in the sense that cells are separated in gel electrophoresis—EQELS is a totally different technique. Platelets are normally negatively charged, and when exposed to an agonist such as ADP, become positively charged. As stated, the platelet's velocity is measured by a Doppler shift. The Doppler shift determines differences in the frequency of coherent light that is incident on the platelet, compared to the frequency of the scattered light. From this difference, the EM is calculated.

Figure 11:
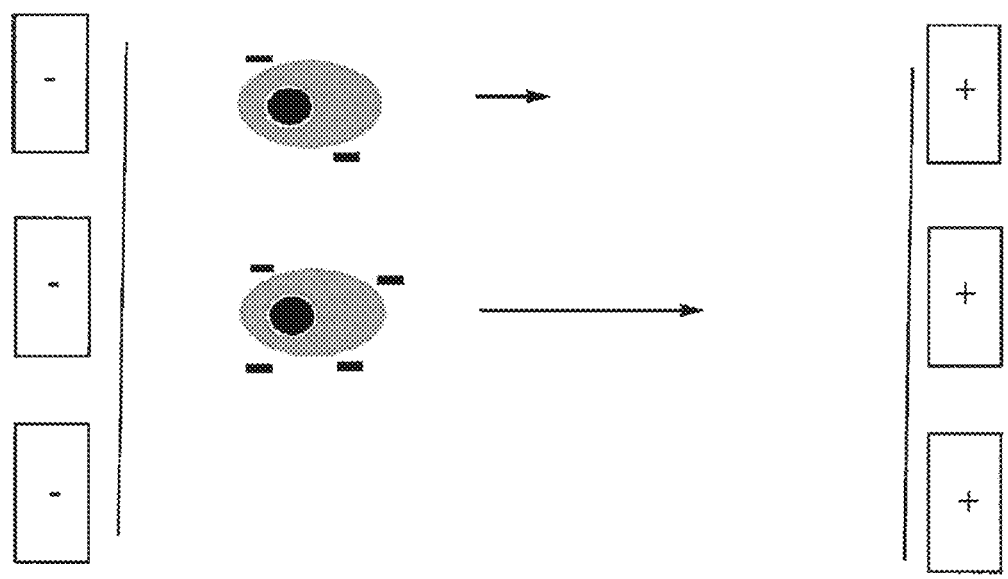
FIG. 11 is a schematic illustration of an electric field generated between 2 electrodes, with a platelet suspended in the electric field.

As shown in FIG. 11, one first creates an electric field between 2 electrodes, and then suspends a charged particle (a platelet) in the field. The platelet moves in response to the electric field because of its surface charge. The platelet's mobility changes as its surface charge changes.

When the platelet is activated, such as when a P2Y12 agonist is bound to its surface, its surface charge density changes. Mobility is detected from the Doppler shift of light scattered from the moving platelet. Changes in mobility permit detection of differences in the activation state or changes in the surface caused by drug binding. So, a series of mobilities can be obtained, which provide the desired information. In the case of platelet activation, this enables one to determine whether or not a patient will or will not benefit from a particular anti-thrombotic therapy. That is, if the surface charge changes from negative to positive, the platelet has been activated by the P2Y12 agonist, which indicates that the P2Y12 antagonist was unable to protect the platelet from activation. If the surface charge stays negative, this indicates that the P2Y12 antagonist was able to protect the platelet from activation.

In addition to the P2Y12 receptor, a number of other receptors are involved in platelet activation, adhesion and aggregation. Other anti-thrombotic agents include antagonists (inhibitors) of receptors such as Protease-Activated Receptor 1 (PAR1), Protease-Activated Receptor 4 (PAR4), GPIV, Thromboxane receptor (TP receptor, including TP-alpha and TP-beta), vWF antagonists, and Glycoprotein Ib (platelet), alpha polypeptide (GP1BA) also known as CD42b (Cluster of Differentiation 42b), GPIb, antagonists, and Glycoprotein IIb/IIIa (GPIIb/IIIa) antagonists. Terutroban is a representative TP inhibitor. Representative PAR1 inhibitors include SCH 530348, SCH 205831, SCH 602539, and E5555. Representative GP1b inhibitors include vWF, ARC 1779, ALX 0081 and AJW 200. Representative GPIIb/IIIa inhibitors include Abciximab, Eptifibatide, and Tirofiban. In another embodiment of the invention, these inhibitors are also screened using methods analogous to those described above with respect to P2Y12.

Whereas the embodiments related to P2Y12 antagonists involve incubating cells with a P2Y12 antagonist, and exposing the incubated cells to a P2Y12 agonist, these embodiments involve incubating the cells with a PAR1, PAR4, GPIV, TP receptor (including TP-alpha and TP-beta), GPIb, GP1BA, or GPIIb/IIIa antagonist. The incubated cells are then exposed to the corresponding agonists. For PAR1, thrombin is a suitable agonist. For GP-1b, von Willebrand Factor (vWF) is a suitable agonist. For TP receptors, thromboxane A2 (TXA2) is a suitable agonist. The peptide AYPGKF is a representative PAR-4 agonist, which is known to stimulate thromboxane production by human platelets (see, for example, Henrickson and Hanks, Arteriosclerosis, Thrombosis, and Vascular Biology. 2002; 22:861). Fibrinogen is a ligand for GPIIb/IIIa. EP80317 is a representative GPIV agonist.

In addition to determining binding with a routine dosage of an anti-thrombotic agent, one can also determine the effect of differing dosages of anti-thrombotic agents. This is particularly important for those individuals who may be able to take a particular agent, such as Plavix®, but need to be prescribed a higher dosage.

Figure 12:
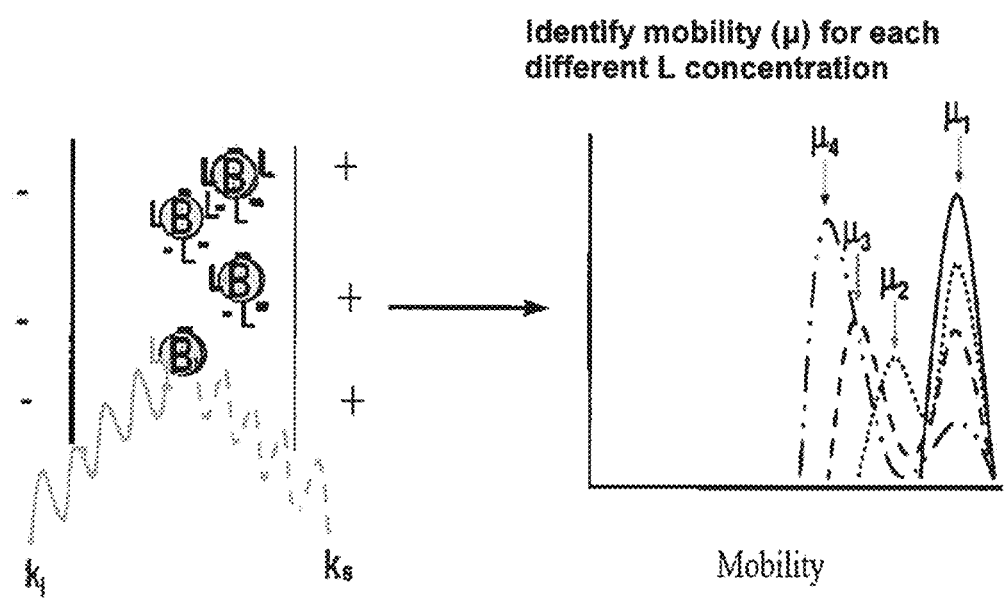
FIG. 12 is a chart showing that one can identify the mobility for a variety of different plasma concentrations of an anti-thrombotic agent, such as Plavix®.

As shown in FIG. 12, one can determine the binding coefficient for a ligand (drug) from the change in mobility of platelets from a biological sample of a patient who has been dosed with different concentrations of an anti-thrombotic agent, after the sample has been exposed to and activated by a P2Y12 agonist. At a first concentration ($\mu 1$; here $\mu$ refers to the platelet mobility after a specific concentration of drug has been added), the platelets, following exposure to ADP, show movement in a direction that correlates to no inhibition of platelet aggregation (i.e., the platelet charge has gone from negative to positive upon exposure to the agonist. However, in successively higher concentrations, ($\mu 2$, $\Xi 3$, and $\mu 4$), the platelets are shown moving, at least in higher concentrations, to the left, which is indicative that the platelets (or a significant number of them) are maintaining their negative surface charge. A physician can then diagnose a patient whose chart shows this trend as one who requires a specific dosage of the anti-thrombotic agent to achieve a desired therapeutic effect.

Figure 13:
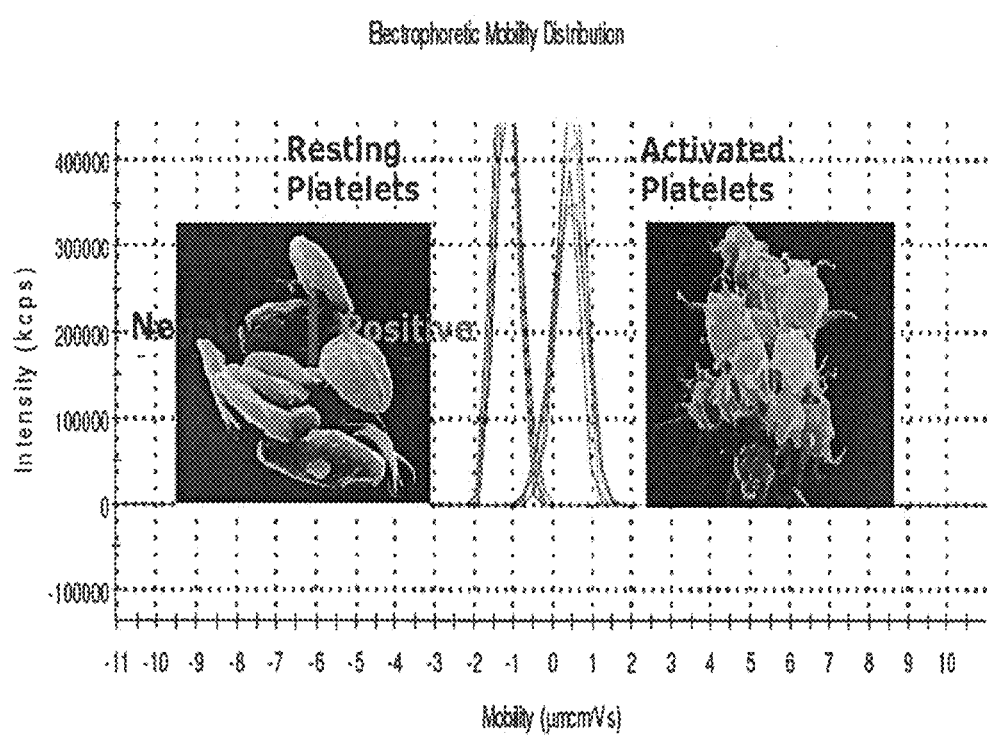
FIG. 13 is a chart showing the signal intensity (kcps) versus particle mobility (μmcm/Vs). The platelets moving to the left of zero mobility are those which retain their negative charge following exposure to a P2Y12 agonist. The platelets moving to the right of zero mobility are those which do not retain their negative charge (i.e., become positively charged) following exposure to a P2Y12 agonist. This figure demonstrates how the assay method can be used to measure the binding of an anti-thrombotic agent to the platelet surface.

FIG. 13 is a chart showing the signal intensity (kcps) versus particle mobility ($\mu m \cdot cm/V \cdot s$). The platelets moving to the left of zero mobility are those which retain their negative charge following exposure to a P2Y12 agonist. The platelets moving to the right of zero mobility are those which do not retain their negative charge (i.e., become positively charged) following exposure to a P2Y12 agonist. This figure demonstrates how the assay method can be used to measure the binding of an anti-thrombotic agent to the platelet surface. FIG. 13 also shows the difference in the platelet surface. As shown in FIG. 13, un-activated platelets have a smooth surface structure, but when activated with an agonist, have a rougher surface structure.

The types of devices that can be used to carry out these diagnostic assays, and methods for performing these assays, are described in more detail below.

I. Focused Light Scattering Devices and Algorithms for Measuring Particle Size and Shape An exemplary apparatus useful for performing the methods described herein is disclosed in U.S. Patent Application Publication No. 20040011975, the contents of which are hereby incorporated by reference in its entirety. The apparatus is described therein is useful in performing particle analysis using focused light scattering techniques. However, as described herein, other similar apparatus can be employed, including detectors for focused light scattering and/or light extinction.

The principal defining characteristic of the focused light scattering method described in U.S. Patent Publication No. 20070010974, the contents of which are hereby incorporated by reference, is not simply a significant reduction in the size of the illuminated area, $A0$, resulting in a significant reduction in VOSZ and improvement in sensitivity. Rather, it concerns the nature of the illuminating beam and the resulting OSZ thereby defined.

The term "focused light scattering" refers to a method for sensing single particles, suspended in a solution, when the solution is passed through a focused beam. When the beam passes through the solution without being scattered by a particle, the beam passes on to a photodetector and the intensity is measured. When the beam is scattered, in whole or in part, by a particle, the intensity of the beam hitting the photodetector is altered. The particle size and concentration can be calculated, for example, using light-extinction, light-scattering detection, or both.

In one embodiment, the beam is produced by a laser. The laser beam interacts with the particles, and produces scattered light when the laser beam interacts with a particle. In one aspect of this embodiment, the apparatus includes two or more different lasers, which can give off light at two or more different wavelengths, and/or which can interact with the particles at different angles. The use of light at different wavelengths can enable one to identify specific epitopes. Particles can interact with specific molecules, including fluorescently-labeled molecules, and the fluorescence can be detected using a laser with light at a predetermined wavelength that interacts with the fluorescent label. The use of more than two lasers can enable the use of two or more fluorescent labels, which labels fluoresce at different wavelengths. This technique is described in more detail below.

A beam of light (usually laser light) of a single wavelength is directed onto a hydrodynamically-focused stream of fluid that includes the platelets. A number of detectors are aimed at the point where the stream passes through the light beam. In one aspect of this embodiment, one detector is in line with the light beam (Forward Scatter or FSC) and one or more detectors are perpendicular to it, including Side Scatter or SSC detectors and one or more fluorescent detectors. Each suspended platelet passing through the beam scatters the ray, and fluorescent chemicals either present within the platelet or attached to the platelet are excited into emitting light at a longer wavelength than the light source. This combination of scattered and fluorescent light is picked up by the detectors, and, by analyzing fluctuations in brightness at each detector (one for each fluorescent emission peak), it is then possible to derive various types of information about the physical and chemical structure of each individual platelet.

Thus, in some embodiments of the apparatus described herein, there are three or more detectors. For example, one can include one detector for extinction [used to measure particles with a size >0.7 microns], one for scattered light [used to measure particles with a size in the range of 0.15 to 0.7 microns] and one or more for fluorescence [used for phenotyping].

The sources of light can include lamps (i.e., mercury, xenon); high-power watercooled lasers (i.e., argon, krypton, dye laser); low-power air-cooled lasers (i.e., argon (488 nm), red-HeNe (633 nm), green-HeNe, HeCd (UV)); diode lasers (i.e., blue, green, red, violet). The detectors can convert fluorescence signals from light into electrical signals that can be processed by a dynamic monitoring system, such as a computer.

Data Acquisition

The process of collecting data from samples is termed "acquisition." Acquisition is typically mediated by a dynamic monitoring system that is used to monitor the size and/or number of particles, and, optionally, additional information on a subset of the particles, such as their number and/or size, which fluoresce when complexed to a particular fluorescent molecule, in a single particle optical sizing device as described herein. When used in connection with EQELS, the dynamic monitoring system can monitor the electrophoretic mobility of particles, rather than monitor their size and/or number.

The monitoring system includes a data acquisition module operatively coupled to the one or more detectors, and (iii) a processing and display unit operatively coupled to the data acquisition module for determining the size and/or number of particles in a given sample and responsively outputting a graphical representation of the size and/or number of the particles in the sample. The data acquisition module uses the data obtained from the detectors in the single particle optical sensing device described herein, and an algorithm which correlates the data to the size and/or number of particles in the sample medium.

The processing and display unit that is coupled to the data acquisition module may utilize any suitable processing means, e.g., a general purpose programmable digital computer or central processing unit (CPU) including memory and processor components. The processor may be arranged to communicate with the memory by means of an address/data bus, and can be constituted by a commercially available or custom microprocessor. The memory can include, without limitation, devices of varied type, such as cache, ROM, PROM, EPROM, EEPROM, flash memory, SRAM, and DRAM.

The memory may include several categories of software and data used in the data processing system: the operating system; the application programs; the input/output (I/O) device drivers and the data. The data may include a database of known profiles of particle sizes, for example, a reference library of the size of platelets, bacteria, viruses, fungi, cancer cells, stem cells, and complexes of the cells with various molecules, including fluorescently-labeled molecules, such as fluorescently-labeled antibodies, and the like.

It will be appreciated that the operating system in the processing and display unit can be of any suitable type for use with a data processing system. Illustrative examples of operating systems that can be usefully employed include, without limitation, OS/2, AIX, OS/390 or System390 (International Business Machines Corporation, Armonk, N.Y.), Windows CE, Windows NT, Windows95, Windows98, Windows2000, or WindowsXP (Microsoft Corporation, Redmond, Wash.), Unix or Linux or FreeBSD, Palm OS from Palm, Inc., Mac OS (Apple Computer, Inc.), LabView or proprietary operating systems. The I/O device drivers typically include software routines accessed through the operating system by the application programs to communicate with devices such as I/O data port(s), data storage and certain components of the memory. The application programs are illustrative of the programs that implement the various features of the system and can suitably include one or more applications that support analysis of the data. The data represent the static and dynamic data used by the application programs, the operating system, the I/O device drivers, and other software programs that may reside in the memory.

Any configuration of the processor capable of carrying out the operations for the methodology of the invention can be advantageously employed. The I/O data port of the processing and display unit can be used to transfer information between the processing and display unit and another computer system or a network (e.g., the Internet) or to other devices controllable by the processor. The processing and display unit optionally, but ideally, includes a display for graphically outputting information on the size and/or number of particles in a sample, in the form of a representation of the sample being assayed and the size and/or number of particles in the sample. This representation may be a graphic depiction, in which the size and/or number of particles are schematically depicted in a graphical output, as a two dimensional column listing the size and/or number of particles, and the like. Such type of depictions can provide an intuitive and readily visually perceptible indication of the size and/or number of particles in the sample.

In one embodiment, the dynamic monitoring system is a computer physically connected to the apparatus, and the software which handles the digital interface with the apparatus, although the computer can receive information from the apparatus via infrared, Bluetooth signals, and the like, and thus need not be physically connected to the device. The software is capable of adjusting parameters (i.e. voltage, compensation, etc.) for the sample being tested, and also assists in displaying initial sample information while acquiring sample data to insure that parameters are set correctly. An interactive database can allow the apparatus to be used in applications for both clinical and research purposes. A wide variety of analysis software and fluorescently-labeled antibodies has been developed, and are well known to those of skill in the art.

The apparatus can include multiple lasers (between 2 and 5, typically between two and four) and fluorescence detectors (typically between 2 and 18, more typically between 2 and 10). Increasing the number of lasers and detectors allows for multiple antibody labeling, and can more precisely identify a target population by their phenotypic markers.

Gating

The data generated by the apparatus can be plotted in a single dimension, in two dimensions, or even in three dimensions. The regions on these plots can be sequentially separated, based on fluorescence intensity, by creating a series of subset extractions, termed "gates." Specific gating protocols exist for diagnostic and clinical purposes especially in relation to hematology. The plots are often made on logarithmic scales. Because different fluorescent dyes' emission spectra overlap, signals at the detectors have to be compensated electronically as well as computationally. Data accumulated using the apparatus can be analyzed using software, e.g., Flowjo, FCS Express, VenturiOne or CellQuest Pro. Data analysis can be performed on a separate data monitoring system, such as a separate computer, if desired.

Computational Analysis

Automated population identification using computational methods can be used as an alternative to traditional gating strategies. Automated identification systems can potentially help find rare and/or hidden populations. Representative automated methods include FLOCK in Immunology Database and Analysis Portal (ImmPort), FLAME in GenePattern and flowClust, in Bioconductor.

Fluorescent Labels

A wide range of fluorophores can be used as labels in flow cytometry. Fluorophores, or simply "fluors", are typically attached to an antibody that recognizes a target feature, epitope, on or in the cell; they may also be attached to a chemical entity with affinity for the cell membrane or another cellular structure. Each fluorophore has a characteristic peak excitation and emission wavelength, and the emission spectra of different labels often overlap. Consequently, the combination of labels which can be used depends on the wavelength of the lamp(s) or laser(s) used to excite the fluorochromes and on the detectors available (Loken MR (1990). Immunofluorescence Techniques in Flow Cytometry and Sorting (2nd ed.). Wiley. pp. 341-53). The maximum number of distinguishable fluorescent labels is thought to be 17 or 18, and this level of plexy necessitates laborious optimization to limit artifacts, as well as complex deconvolution algorithms to separate overlapping spectra (Ornatsky, O.; Bandura, D.; Baranov, V.; Nitz, M.; Winnik, M. A.; Tanner, S. (2010). "Highly multiparametric analysis by mass cytometry". Journal of Immunological Methods 361 (1-2): 1-20) Quantum dots are sometimes used in place of traditional fluorophores because of their narrower emission peaks.

The fluorescent labels can be used, for example, to determine the degree of protein expression and localization, the existence of any protein modifications or intracellular antigens (various cytokines, secondary mediators, etc.), membrane fluidity, platelet viability, and platelet adherence.

Representative fluorescent labels are provided below:

| Probe | Ex (nm) | Em (nm) |
|---|---|---|
| Hydroxycoumarin | 325 | 386 |
| Aminocoumarin | 350 | 445 |
| Methoxycoumarin | 360 | 410 |
| Cascade Blue | (375); 401 | 423 |
| Pacific Blue | 403 | 455 |
| Pacific Orange | 403 | 551 |
| Lucifer yellow | 425 | 528 |
| NBD | 466 | 539 |
| R-Phycoerythrin (PE) | 480; 565 | 578 |
| PE-Cy5 conjugates | 480; 565; 650 | 670 |
| PE-Cy7 conjugates | 480; 565; 743 | 767 |
| Red 613 | 480; 565 | 613 |
| PerCP | 490 | 675 |
| TruRed | 490, 675 | 695 |
| FluorX | 494 | 520 |
| Fluorescein | 495 | 519 |
| BODIPY-FL | 503 | 512 |
| TRITC | 547 | 572 |
| X-Rhodamine | 570 | 576 |
| Lissamine Rhodamine B | 570 | 590 |
| Texas Red | 589 | 615 |
| Allophycocyanin (APC) | 650 | 660 |
| APC-Cy7 conjugates | 650; 755 | 767 |
| Alexa Fluor 350 | 343 | 442 |
| Alexa Fluor 405 | 401 | 421 |
| Alexa Fluor 430 | 434 | 540 |
| Alexa Fluor 488 | 499 | 519 |
| Alexa Fluor 500 | 503 | 525 |
| Alexa Fluor 514 | 517 | 542 |
| Alexa Fluor 532 | 530 | 555 |
| Alexa Fluor 546 | 561 | 572 |
| Alexa Fluor 555 | 553 | 568 |
| Alexa Fluor 568 | 579 | 603 |
| Alexa Fluor 594 | 591 | 618 |
| Alexa Fluor 610 | 610 | 629 |
| Alexa Fluor 633 | 632 | 648 |
| Alexa Fluor 647 | 652 | 668 |
| Alexa Fluor 660 | 663 | 691 |
| Alexa Fluor 680 | 680 | 702 |
| Alexa Fluor 700 | 696 | 719 |
| Alexa Fluor 750 | 752 | 776 |
| Alexa Fluor 790 | 782 | 804 |
| Cy2 | 489 | 506 |
| Cy3 | (512); 550 | 570; (615) |
| Cy3B | 558 | 572; (620) |
| Cy3.5 | 581 | 594; (640) |
| Cy5 | (625); 650 | 670 |
| Cy5.5 | 675 | 694 |
| Cy7 | 743 | 767 |
| DyLight 350 | 353 | 432 |
| DyLight 405 | 400 | 420 |
| DyLight 488 | 493 | 518 |
| DyLight 549 | 562 | 576 |
| DyLight 594 | 593 | 618 |
| DyLight 633 | 638 | 658 |
| DyLight 649 | 654 | 673 |
| DyLight 680 | 692 | 712 |
| DyLight 750 | 752 | 778 |
| DyLight 800 | 777 | 794 |
| Hoechst 33342 | 343 | 483 |
| DAPI | 345 | 455 |
| Hoechst 33258 | 345 | 478 |
| SYTOX Blue | 431 | 480 |
| Chromomycin A3 | 445 | 575 |
| Mithramycin | 445 | 575 |
| YOYO-1 | 491 | 509 |
| Ethidium Bromide | 493 | 620 |
| Acridine Orange | 503 | 530/640 |
| SYTOX Green | 504 | 523 |
| TOTO-1, TO-PRO-1 | 509 | 533 |
| Thiazole Orange | 510 | 530 |
| Propidium Iodide (PI) | 536 | 617 |
| LDS 751 | 543; 590 | 712; 607 |
| 7-AAD | 546 | 647 |
| SYTOX Orange | 547 | 570 |
| TOTO-3, TO-PRO-3 | 642 | 661 |
| DRAQ5 | 647 | 681, 697 |
| Indo-1 | 361/330 | 490/405 |
| Fluo-3 | 506 | 526 |
| DCFH | 505 | 535 |
| DHR | 505 | 534 |
| SNARF | 548/579 | 587/635 |
| Y66H | 360 | 442 |
| Y66F | 360 | 508 |
| EBFP | 380 | 440 |
| EBFP2 | 383 | 448 |
| Azurite | 383 | 447 |
| GFPuv | 385 | 508 |
| T-Sapphire | 399 | 511 |
| TagBFP | 402 | 457 |
| Cerulean | 433 | 475 |
| mCFP | 433 | 475 |
| ECFP | 434 | 477 |
| CyPet | 435 | 477 |
| Y66W | 436 | 485 |
| dKeima-Red | 440 | 616 |
| mKeima-Red | 440 | 620 |
| TagCFP | 458 | 480 |
| AmCyan1 | 458 | 489 |
| mTFP1 (Teal) | 462 | 492 |
| S65A | 471 | 504 |
| Midoriishi-Cyan | 472 | 495 |
| Wild Type GFP | 396, 475 | 508 |
| S65C | 479 | 507 |
| TurboGFP | 482 | 502 |
| TagGFP | 482 | 505 |
| TagGFP2 | 483 | 506 |
| AcGFP1 | 484 | 510 |
| S65L | 484 | 510 |
| Emerald | 487 | 509 |
| S65T | 488 | 511 |
| EGFP | 488 | 507 |
| Azami-Green | 492 | 505 |
| ZsGreen1 | 493 | 505 |
| Dronpa-Green | 503 | 518 |
| TagYFP | 508 | 524 |
| EYFP | 514 | 527 |
| Topaz | 514 | 527 |
| Venus | 515 | 528 |
| mCitrine | 516 | 529 |
| YPet | 517 | 530 |
| TurboYFP | 525 | 538 |
| PhiYFP | 525 | 537 |
| PhiYFP-m | 525 | 537 |
| ZsYellow1 | 529 | 539 |
| mBanana | 540 | 553 |
| Kusabira-Orange | 548 | 559 |
| mOrange | 548 | 562 |
| mOrange2 | 549 | 565 |
| mKO | 548 | 559 |
| TurboRFP | 553 | 574 |
| tdTomato | 554 | 581 |
| DsRed-Express2 | 554 | 591 |
| TagRFP | 555 | 584 |
| DsRed monomer | 557 | 592 |
| DsRed2 ("RFP") | 563 | 582 |
| mStrawberry | 574 | 596 |
| TurboFP602 | 574 | 602 |
| AsRed2 | 576 | 592 |
| mRFP1 | 584 | 607 |
| J-Red | 584 | 610 |
| mCherry | 587 | 610 |
| HcRed1 | 588 | 618 |
| mKate2 | 588 | 633 |
| Katushka (TurboFP635) | 588 | 635 |
| mKate (TagFP635) | 588 | 635 |
| TurboFP635 | 588 | 635 |
| mPlum | 590 | 649 |
| mRaspberry | 598 | 625 |
| mNeptune | 600 | 650 |

| Probe | Ex (nm) | Em (nm) |
| --- | --- | --- |
| E2-Crimson | 611 | 646 |
| Monochlorobimane | 380 | 461 |
| Calcein | 496 | 517 |

In some applications, particularly clinical applications, it can be desirable to use microfluidics to introduce samples to the apparatus. The microfluidic device can be disposable (i.e., used once or perhaps a few times, followed by disposal and replacement) and/or composed of a polymeric material. The microfluidic device can be adapted to reduce the amount of sample used to determine whether a patient can benefit from a particular anti-thrombotic therapy. The microfluidic device preferably provides a tip adapted for delivering the biological sample including the platelets into the cell through which light passes, so that the platelets can then travel through the light beam(s). In some embodiments, the tip is adapted for sheath spraying. In other embodiments, the tip is adapted for non-sheath spraying. In any of the embodiments herein the apparatus may include a disposable inlet capillary.

The apparatus can also include an autodiluter, which can start with the most dilute sample, rather than the most concentrated sample, and can therefore use less sample. Autodiluters are well known to those of skill in the art. Representative autodiluters include the AutoDiluter-5.2, the CETAC ADX-500 Autodiluter, the ProLiquid AutoDiluter, and the DYNATECH Autodiluter III.

In high-throughput screening, it can be preferable to include robotics, which can introduce the samples to the apparatus. Ideally, the apparatus can then be cleaned in between samples, for example, by flushing the various lines, and subsequent samples introduced, enabling the screening to be automated. Information on the screening results can be stored, for example, in a memory map, and the information correlated with the patient's identity.

A "focused light scattering device" is a single-particle optical sensor, which has high sensitivity and responds to relatively concentrated suspensions, uses a relatively narrow light beam to illuminate an optical sensing zone non-uniformly. It differs from conventional SPOS devices in that it can handle more concentrated solutions and smaller particle sizes.

In use, a solution including suspended platelets passes through a zone. The zone is smaller than the flow channel, so that the sensor responds to only a fraction of the total number of platelets flowing through the channel, detecting a statistically significant number of particles of any relevant diameter.

Because different particle trajectories flow through different parts of the zone illuminated at different intensities, it is necessary to deconvolute the result. Two methods of deconvolution can be used: modified matrix inversion or successive subtraction. Both methods use a few basis vectors measured empirically or computed from a theoretical model, and the remaining basis vectors are derived from these few. The sensor is compensated for turbidity.

The sensor apparatus for single-particle optical sizing of particles in a fluid suspension typically includes a means for establishing flow of the suspension through a physically well-defined measurement flow channel. There is also an illumination means for effectively directing a relatively narrow beam of light, having an axis, through the measurement flow channel to form an optical sensing zone within the measurement flow channel. The beam of light and the optical sensing zone are of such size relative to the size of the measurement flow channel that the sensor apparatus responds to only a fraction of the total number of particles flowing through the measurement flow channel. In this manner, the sensor apparatus responds effectively to a relatively concentrated fluid suspension.

The beam has a maximum intensity portion and a continuum of lesser intensities for positions spaced transverse to the axis from the maximum intensity portion. In this manner, some of the particles have trajectories through the maximum intensity portion, others of the particles have trajectories through the lesser intensity positions, and still others of the particles may have trajectories outside the zone. Typically, the maximum intensity portion of the beam is in a central portion of the beam. The device also includes a detector means for photo-detecting light from the zone to provide pulse height signals. These signals each respond to a particle flowing through the zone. The pulse height signals are functions of the sizes and trajectories of detected particles. Particles of a given size provide a maximum pulse height signal when flowing through the maximum intensity portion, and lesser pulse height signals when flowing through the lesser intensity positions of the zone. The pulse height signals, collectively, form a pulse height distribution PHD.

The device further includes a means for mathematically deconvoluting the pulse height distribution to extract a particle size distribution of the PSD particles in the fluid suspension. The sensor apparatus can detect a statistically significant number of particles of any given diameter or range of diameters that are relevant to the fluid suspension.

In one embodiment, the measurement flow channel has a thickness dimension axially of the beam of light, a width dimension transverse to the beam, and a flow direction substantially perpendicular to the thickness and width dimensions. The beam is narrower than the measurement flow channel in the width direction. The beam can be focused with a depth of field which is substantially larger than the thickness dimension, and the beam substantially has an effective width which does not vary substantially over the thickness dimension.

In another embodiment, the beam has an effective width between opposing positions transverse to the axis in the beam, at which the lesser intensities have fallen to a given fraction of the maximum intensity. The effective width is chosen so that the largest particles of interest can be effectively sized. The given fraction can be, for example, 1/e2 of the maximum intensity, where e is the base of the natural system of logarithms, and the effective width is substantially one half the size of the largest particle to be sized.

In yet another embodiment, the apparatus uses hydrodynamic sample injection, such as is described in Pelssers et al., Journal of Colloid and Interface Science, Volume 137, Issue 2, July 1990, Pages 350-361. Colloidal dispersions, such as platelets in serum or other media, can be hydrodynamically focused laser. into a narrow stream, with widths ranging from about 3 to about 10, preferably about µm width. The use of a focused light scattering technique allows one to measure relatively small particle sizes. However, where a focused beam hits particles in a relatively wide sample stream (as described above, where the beam is narrower than the measurement flow channel in the width direction), the detection method relies somewhat on statistics. That is, where the beam is substantially narrower than the sample stream, an assumption is made that there is an equal distribution of particles in the sample stream, so that one can extrapolate the results of the interaction of the light in the narrow beam with the particles in its path over the entire width of the sample stream. By hydrodynamically focusing the sample into a stream with a relatively narrow width, and using a focused light source, it is possible to count all or most of the particles in the sample stream, and rely to a lesser extent on statistics.

The light beam can have, for example, a Gaussian intensity profile, a circular cross-section, or an elliptical cross-section being wider in a direction transverse to particle flow. The detector means can be include a light extinction-type detector, and can be a combination of detectors, for example, a light-extinction detector type and a light scattering type detector. The light-scattering type detector means can include means for passing a portion of scattered light from the zone through a mask to select light scattered between a first and a second angle to the beam and a means for directing a portion of the light transmitted through the zone to a light-extinction type detector.

The detector means can include a mirror for deflecting a portion of the light from the optical-sensing zone to the light-extinction detector. The illuminating means can include a light source and optical fiber means for conveying light from the light source to the optical sensing zone, and projecting the light through the zone. The detector means can also include an optical fiber means for conveying the light passing through the optical sensing zone to the light-extinction type detector. The detector means can also include means for passing a portion of the light scattered from the zone through a mask, to select light scattered between a first and second angle to the beam, and an optical fiber means for conveying the portion of the light to a light scattering type detector. The detector means can also include a light-scattering detector.

In one embodiment, the illumination means provides two light beams directed through a pair of optical sensing zones positioned within the measuring flow channel, and each beam has an effective width determined by a desired maximum particle size.

The detector means can include a light-scattering detector and a means for passing light scattered from the zone through a mask means. The mask means can include a plurality of masks and means for selecting one of the masks for passing the light scattered from the zone, each mask defining different angles between which the light is scattered.

The masks can be located on a rotatable wheel, and a mask can be selected by rotating the wheel to a desired position.

The illuminating means can project a relatively wide collimated beam through the optical sensing zone, and can include an acceptance aperture to capture only those light rays that closely surround the axis of the beam. This reduces the effective width of the beam to a width in a direction transverse to the axis of the light beam which is substantially one-half the size of the largest particle to be sized. The illuminating means can also include a means for coupling the light rays to the detector means. This can be, for example, an optical fiber means.

In one aspect of the invention, a statistically significant number of particles of each relevant size flow through all portions and positions of the zone.

In another aspect of the invention, the fluid suspension is relatively concentrated and the apparatus further comprises means to compensate for turbidity of the suspension.

In this aspect, the detector means can operate on a light extinction principle, and provide a signal having a baseline voltage level. The pulse height signals appear as downwardly extending pulses from the baseline voltage level, and the means for compensation for turbidity of the suspension can include means to sense the baseline voltage level and automatically increase the level to approximately the baseline voltage level present in the absence of turbidity in the suspension. The detector means can operate on a light extinction principle, and provide a signal having a baseline voltage level, wherein the means to compensate for turbidity can include a computer means for correcting the pulse height signals in response to the ratio of the baseline voltage level when the fluid suspension is not turbid, to the baseline voltage level for the turbid fluid suspension. The detector means can also operate on a light extinction principle and provide a signal having a baseline voltage level, wherein the means to compensate for turbidity includes a means to adjust the intensity of the beam of light by increasing the amount of light produced by the illuminating means in response to the ratio of the baseline voltage level when the fluid suspension is not turbid, to the baseline voltage level for the turbid fluid suspension.

The particle trajectories can be substantially uniformly distributed across the width of the measurement flow channel. The means for deconvoluting the pulse height distribution can include basis vectors, each corresponding to a particular particle size, and a source vector representing a measured pulse height distribution for a fluid suspension as detected by the detector means. There can also be a means using a deconvolution algorithm to derive the particle size distribution from the pulse height distribution. At least some of the basis vectors can have values based upon measurements of particles of known size. Some of the basis vectors can also have values based upon measurements of particles of known size and others of the basis vectors can be computed from the sum of the basis vectors by interpolation and/or extrapolation.

The basis vectors can be computed, and the basis vectors can be column basis vectors of a matrix, where the means using a deconvolution algorithm performs matrix inversion and vector multiplication, or the means using a deconvolution algorithm can perform successive subtraction.

The means using a deconvolution algorithm can provide a deconvoluted pulse height distribution dPHD, and the apparatus further comprises means providing a calibration curve of the relationship of pulse height and diameter, and means using the calibration curve to transform each deconvoluted pulse height value in the dPHD into a unique particle diameter associated with this pulse height value. This can yield a "raw" particle size distribution PSD. There can also be a means for converting the raw PSD into a final PSD by renormalizing the raw PSD by multiplying by the value 1/PHId, where PHId is the fraction of particles actually detected by the device for particles of each size.

The particle trajectories can be distributed non-uniformly across the width of the measurement flow channel, and the basis vectors can be based upon the response of particles of known size flowing through the measurement flow channel with the same non-uniform distribution of particle trajectories as the fluid suspension.

The sensor apparatus may respond only to a fraction of the total number of particles flowing through the measurement flow channel. One can prepare a matrix for deconvoluting pulse height distributions derived from particles of unknown size flowing along different trajectories through a non-uniform light field of a single-particle optical sizing device. This can enable one to size particles in a fluid suspension. To do this, one can determine the value of at least one empirical basis vector for the matrix by measuring the response of particles of known size flowing through the single-particle optical sizing device. Then, one can compute other basis vectors for the matrix corresponding to particles of other sizes, by interpolating and/or extrapolating the other basis vectors from the empirical basis vector. One can also determine the value of additional empirical basis vectors for the matrix by measuring the response of particles of known sizes flowing through the single particle optical sizing device, and computing the other basis vectors for the matrix corresponding to particles of other sizes from the at least one empirical basis vector and the additional empirical basis vectors.

Another way to prepare a matrix for deconvoluting pulse height distributions derived from particles of unknown size flowing along different trajectories through a non-uniform light field of a single-particle optical sizing device for sizing particles in a fluid suspension involves determining the value of at least one computed basis vector corresponding to particles of at least one size for the matrix. One can compute other basis vectors for the matrix corresponding to particles of other sizes from computed basis vectors.

Also disclosed is a method of deconvoluting a pulse height distribution derived from particles of unknown size flowing along different trajectories through a non-uniform light field of a single-particle optical sizing device for sizing particles in a fluid suspension. The method involves setting up a matrix having a plurality of columns, each containing a basis vector comprising a pulse height distribution of particles of a known size corresponding to the response of a photo-detector of the device to the particles of known size. Each successive column contains a basis vector for particles of successively larger sizes. The matrix also has a like plurality of rows, each corresponding to a successive pulse height channel, each channel including a range of pulse heights, with successive rows corresponding to successively larger pulse heights, and with each column having a maximum count pulse height value at a location for a row which relates to a pulse height corresponding to the particle of known size associated with the column.

The maximum count pulse height values for successive columns are arranged on a diagonal of the matrix. The matrix is modified by setting all terms corresponding to pulse height values greater than the maximum count pulse height value in a column to zero. A deconvolution algorithm is used to perform matrix inversion and vector multiplication of the pulse height distribution and the matrix as modified. Before the modifying step, one can renormalize the values of the basis vectors in the columns by setting the maximum count pulse height value to equal 1.0 and all other count pulse height values in the column to a value maintaining the same proportionate value to 1.0 that the other count pulse height values had to the maximum count pulse height value of the column.

The response of the photo-detection to the particles of known size is developed empirically for some of the basis vectors by sending particles of the substantially known size through the device and providing a response by the device to the particles of known size. The response to the photo-detector for the remaining basis vectors can be computed by interpolating and/or extrapolating the response for the remaining basis vectors from the some of basis vectors.

The response of the photo-detector to the particles of known size can be computed for some of the basis vectors and the response to the photo-detector for the remaining basis vectors can be computed by interpolating and/or extrapolating the response from the some basis vectors.

A pulse height distribution ("PHD") can be derived from particles of unknown size flowing along different trajectories through a non-uniform light field of a single particle optical sizing device for sizing particles in a fluid suspension can be deconvoluted by setting up a matrix having a plurality of columns. Each column includes a basis vector comprising a pulse height distribution of particles of a substantially known size corresponding to the response of a photo-detector of the device to the particles of known size, and each successive column contains a basis vector for particles of successively larger sizes. The matrix can also include a like plurality of rows, each corresponding to a successive pulse height channel, each channel including a range of pulse heights, successive rows corresponding to successively larger pulse heights, each column having a maximum count pulse height value at a location for a row which relates to a pulse height corresponding to the particle of known size associates with the column.

The maximum count pulse height values for successive columns can be arranged on a diagonal of the matrix. A successive subtraction algorithm can be implemented, by starting with the basis vector with its maximum count value in the largest row number; scaling a column basis vector by a factor corresponding to the value of the row in the PHD that matches the column number; subtracting the scaled basis vector from the PHD to form an element of a deconvoluted PHD (dPHD), leaving an intermediate PHD vector with a smaller number of total particles; and repeating this process using the remaining basis vectors until the entire PHD has been consumed and all the elements of the deconvoluted dPHD have been formed.

A single-particle optical sizing sensor for sizing particles in a relatively concentrated fluid suspension sample for turbidity of the suspension sample can be compensated using a sensor operating on a light extinction principle whereby a photodetector produces signal $V_{LE}(t)$ having a baseline voltage level and a response to blockage of light by a particle as a downwardly extending pulse from the baseline voltage level. The compensation method involves passing a non-turbid suspension through the sensor; measuring a baseline voltage level $V_0$ produced in response to the non-turbid suspension; passing the relatively concentrated suspension sample through the sensor; measuring a baseline voltage $V_0^T$ produced in response to the relatively concentrated suspension sample, calculating the ratio $V_o V_0^T$; and adjusting the sensor in response to G to compensate for the turbidity when the relatively concentrated suspension sample passes through the sensor. The baseline voltage $V_0^T$ can effectively be subtracted from the signal $V_{LE}(t)$, the remaining signal can be inverted to produce a pulse height signal 2 $V_{LE}^T(t)$, and an adjustable gain amplifying means can be used to amplify the pulse height signal 3 $V_{LE}^T(t)$. The adjustable gain amplifying means can be controlled by the ratio G to provide a compensated pulse height signal $\Delta V_{LE}(t)$.

The signal $V_{LE}(t)$ produced by the sensor in response to the relatively concentrated suspension sample can be amplified by adjustable gain amplifier means, the gain of which is controlled by the ratio G to provide a compensated signal $V_{LE}(t)$ having a compensated baseline voltage V0, subtracting the baseline voltage V0 from the compensated signal $V_{LE}(t)$, and inverting the remaining signal to produce compensated pulse height signal $\Delta V_{LE}(t)$.

In one embodiment, the single-particle optical sizing sensor comprises a light source producing a light beam of adjustable intensity, wherein the intensity is increased in response to the ratio G to compensate for the turbidity.

Particles in a fluid suspension can also be optically sized by establishing a flow of the suspension through a physically well-defined measurement flow channel of a single particle optical sizing sensor apparatus wherein a beam of light, having an axis, is directed through the measurement flow channel to form an optical sensing zone within the measurement flow channel. The beam of light and the optical sensing zone are ideally of such size relative to the size of the measurement flow channel that the sensor apparatus responds to only a fraction of the total number of particles flowing through the measurement flow channel. The sensor apparatus can respond effectively to a relatively concentrated fluid suspension. The beam can have a maximum intensity portion in the beam and a continuum of lesser intensities for positions in the beam spaced transversely from the axis, whereby some of the particles have a trajectory through the maximum intensity portion, others of the particles have trajectories through the lesser intensity positions, and still others of the particles may have trajectories outside the zone. Light from the zone can be detected to provide pulse height signals, each responsive to a particle flowing through the zone. The pulse height signals are functions of the sizes and trajectories of detected particles, and the pulse height signals collectively form a pulse height distribution PHD. The PDH can be mathematically deconvoluted and processed to extract from the PHD a particle size distribution PSD of the particles in the fluid suspension.

The step of mathematically deconvoluting the PHD can involve determining the value of at least one empirical basis vector by measuring the response to particles of known size flowing through the single-particle optical sizing device. Other basis vectors corresponding to particles of other sizes can be computed by interpolating and/or extrapolating the other basis vectors from the empirical basis vector.

The value of additional empirical basis vectors for particles of known sizes flowing through the single-particle optical sizing device can be determined; and the other basis vectors for the matrix corresponding to particles of other sizes can be calculated by interpolating and/or extrapolating the other basis vectors from at least one empirical basis vector and the additional empirical basis vectors. The method can further involve determining the value of at least one computed basis vector corresponding to particles of at least one size. Other basis vectors corresponding to particles of other sizes can also be computed by interpolating and/or extrapolating the other basis vectors from computed basis vectors.

The step of deconvoluting and processing the PHD can involve setting up a matrix having a plurality of columns, each containing a basis vector comprising a pulse height distribution of particles of a known size corresponding to the response of a photodetector of the device to the particles of known size, each successive column containing a basis vector for particles of successively larger sizes. The matrix can also have a like plurality of rows, each corresponding to a successive pulse height channel, each channel including a range of pulse heights, successive rows corresponding to successively larger pulse heights, each column having a maximum count pulse height value at a location for a row which relates to pulse heights corresponding to the particle of known size associated with the column. The maximum count pulse height values for successive columns can be arranged on a diagonal of the matrix. The matrix can be modified by setting all terms corresponding to pulse height values greater than the maximum count pulse height value in a column to zero. A deconvolution algorithm can be used to perform matrix inversion and vector multiplication of the pulse height distribution and the inverted matrix as modified. The response of the photodetector to the particles of known size can be developed empirically for some of the basis vectors by directing a flow of particles of the known size through the device and providing a response by the device to the particles of known size. The response to the photo-detector for the remaining basis vectors can be calculated by interpolating and/or extrapolating the response for the remaining basis vectors from the some of basis vectors.

The step of mathematically deconvoluting the PHD can also involve using a deconvolution algorithm to provide a deconvoluted pulse height distribution dPHD. The method can further involve providing a calibration curve of the relationship of pulse height and diameter, and using the calibration curve to translate each deconvoluted pulse height value in the dPHD into a unique particle diameter associated with this pulse height value yielding a "raw" particle size distribution in PSD. The raw PSD can be converted into a final PSD by renormalizing the raw PSD by multiplying by the value 1/PHId, where PHId is the fraction of particles actually detected by the device for particles of each size.

In use, a focused laser light beam passes through a chamber through which fluid flows, and the laser light scatters as the particles pass through the focused laser beam. An extinction detector determines when particles have passed through the beam. In the absence of a particle interfering with the beam of light, the light would pass, uninterrupted, to the extinction detector. When a particle blocks the passage of light, the resulting loss of light hitting the extinction detector signals that a particle has passed through the beam. The light hitting the particles is reflected, and passed through a scatter collimating lens, which re-focuses the light, which then passes through a scatter focus lens, which sends a single beam through to a scatter detector.

A representative focused light scattering device is shown in FIG. 1. A first laser (1) emits light at a first wavelength, and a second laser (2) emits light at a second wavelength. Both beams of light pass through a first beam splitter (3) and through a first focusing lens (4) before they enter into a flow cell (15). The flow cell includes a site (5) for hydrodynamic injection of the sample. As the platelets in the flow cell pass through the beams of light, the light is scattered as it hits the platelets. The scattered light passes through a circular spatial filter (6) and then through a first collimating lens (7). The light beam passes through a second beam splitter (16), which splits the light into two beams. A first beam passes through a second focusing lens (8) and through a first chromatic filter (9) that passes scattered light from the first laser (1) through a first detector (10). The second beam passes through a second collimating lens (11), a third focusing lens (12) and a second chromatic filter (13) that passes scattered light from the second laser (2) to a second detector (14).

The two photodetectors (10 and 14) each are able to detect light at a certain frequency, so that light transmitted at different frequencies (as a result of the two lasers hitting particles, and which may interact with fluorescent tags on the particles) can be separately determined.

Figure 2:
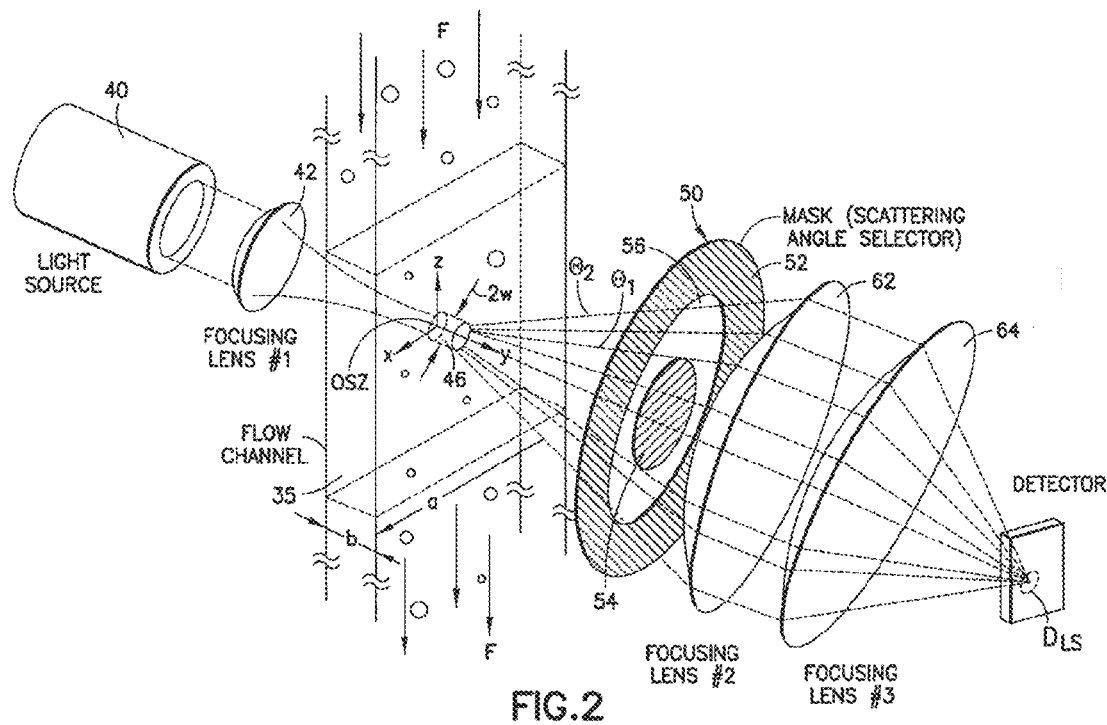
FIG. 2 is a schematic illustration of a device used for focused light scattering, using a single light source and a single detector.

A third detector (an extinction detector) (18) receives a portion of the light passing through the flow cell. A portion of the light passing through the flow cell is reflected off of a movable mirror (17) and onto the third detector. As is shown in FIG. 2, there are two important features inherent in the optical design. First, the incident beam alone (in conjunction with the front and back windows 36 and 37 of the measurement flow channel 35) defines the OSZ. The side walls 38 and 39 that confine the fluid-particle suspension along the x-axis are no longer of any consequence with respect to definition of the OSZ. Second, the physical volume associated with the OSZ can no longer be described by a single value; rather, it now depends on the size of the particles being measured.

The approach shown schematically in FIG. 2 involves illuminating measurement flow channel 35 with a light beam 41 from a laser light source 40 which is focused by a lens 42 to form a beam 44 of relatively narrow cross section—i.e., smaller than. a typical illuminated width, a, of the flow cell in a conventional LE-type sensor.

The resulting OSZ is therefore defined approximately by a "pencil" beam of light 46, together with the front and back windows of the flow cell, separated by dimension "b." The schematic diagram in FIG. 2 provides a simplified picture of the OSZ defined by focused light beam 46. First, the region of illumination that comprises the OSZ is not sharply defined, as implied by the approximately cylindrical zone indicated in FIG. 1. Rather, the outer boundary of the OSZ is "fuzzy," extending well beyond the zone indicated, as discussed below. Second, the beam passing through the flow channel 10, assuming that it has been focused, typically is not uniform in width. Rather, in the case of a focused beam, its width varies over the depth of the measurement flow cell 35. The extent to which the beam waist varies over the depth of the channel depends on the depth of field of the focused beam, defined as the distance (y-axis) between the points at which the beam waist grows to 2 times its minimum value. Ideally, the depth of field is significantly greater than the channel thickness, b, resulting in a relatively uniform beam width throughout the flow channel.

Consequently, focused light scattering devices may include a fundamentally different sensor. In the conventional design, the physical width of the flow channel 10 and the effective width (x-axis) of the OSZ are one and the same, equal to dimension "a."

By contrast, the physical width of the flow channel in a sensor used for focused light scattering devices (also defined as "a") is typically much larger than the nominal width, 2w, of the incident light beam and therefore has no significant influence on the OSZ. Hence, the spacers (or shims) 38 and 39 that separate the front and back windows 36 and 37, determining the depth, b, of the flow cell (and OSZ), no longer need to be opaque or smooth on an optical scale to avoid scattering by the edges. This is a significant advantage, making fabrication of the flow cell easier and less expensive.

It is usually convenient and effective to employ a "circularized" light beam, in which the incident intensity ideally depends only on the radial distance, r, from the beam axis (coincident with the y-axis, with x=z=0, as seen in FIG. 1). Typically, one employs a "Gaussian" light beam—i.e. one having a Gaussian intensity profile, described in the focal plane (minimum beam waist), at y=b/2, by hr)=I0exp(−2r2/w2) (7) where r2=x2+z2 for the assumed circular beam. Quantity 2w is the diameter of an imaginary cylinder containing most of the incident light flux. The intensity on its surface equals 1/e2, where e is the base for natural logarithms, or 0.135 times its value, I0, at the center of the beam (r=0). Essentially 100% (apart from losses due to reflections at optical interfaces and extinction by particles in the beam) of the light flux contained in the incident beam traverses the fluid-particle mixture in the flow channel and impinges on the distant detector $D_{LE}$. This causes detector $D_{LE}$ to provide a light extinction signal $V_{LE}$ in the form of a downwardly extending pulse. This behavior is in sharp contrast to the illumination scheme employed in a conventional LE-type sensor. There, the starting light beam is expanded greatly along the lateral (x) axis of the flow cell, so that its width (1/e2 intensity) is much larger than the width, a, of the front window (and OSZ). As a result, there is relatively little variation in the incident intensity along the x-axis (i.e. for y=z=0) where the beam enters the flow cell, because the light is captured at the top of the x-expanded Gaussian beam. Therefore, a particle passing through the OSZ will experience substantially the same maximum beam intensity (i.e. at z=0), regardless of its trajectory. The specific values of x and y defining the trajectory ideally have no influence on the resulting sensor response, i.e. the pulse height.

There is a sharp contrast between the conventional optical design and the scheme employed in the sensor used for focused light scattering devices. There is a large variation in the incident intensity as a function of position (x-axis) across the width of the flow channel. In the case in which the incident light beam has a symmetric (circular) Gaussian profile, the intensity variation is given by Equation 7, with r=x. The maximum intensity, JO, is achieved at the center of the beam (x=0), where for simplicity x=0 represents the midpoint of the channel (with the side walls at x=±a/2). As noted, the intensity occurring at x=±w, z=0 is reduced substantially, to 0.135 I0. The intensity drops steeply with increasing distance from the beam, falling, for example, to 0.018 10 at x=±2w, z=0 and 0.00033 10 at x=±4 w, z=0.

The consequences for the light-extinction signal thus generated by the passage of particles through the new OSZ are far-reaching. First, as for a conventional LE-type sensor, the pulse height, $\Delta V_{LE}$, generated by passage of a particle through the OSZ in general increases with increasing particle size, all other factors being equal. In general, the larger the particle, the larger the fraction of light "removed" from the incident beam, thus unable to reach the detector DLE. However, with the new sensor the fraction of light removed from the beam now depends on the precise trajectory of the particle—specifically, the minimum distance, |x|, of the particle to the center of the beam, x=0. (To first approximation, the response of the sensor will not vary significantly with changes in the y-axis value of the trajectory, assuming that the beam width is approximately constant over the depth of the flow channel, given an appropriately large depth of field, as discussed above.)

For a particle of given size and composition (hereinafter assumed to be spherical and homogeneous, for simplicity), the maximum "signal," or pulse height, is achieved when the particle passes through the center of the beam, x=0. A particle of given effective cross-sectional area, $\Delta A$, blocks the largest amount of incident light at the center of the beam, where the intensity is greatest. Particles of identical size that pass through the flow channel along different trajectories, with different minimum distances, |x|, from the beam axis, are exposed to varying, but smaller, maximum levels of illumination.

The greater the distance from the beam axis, the lower the integrated intensity incident on a particle and, hence, the less light flux removed from the beam, and the smaller the resulting pulse height. The response therefore consists of a continuous "spectrum" of pulse heights, ranging from a maximum value, for trajectories that pass through the center of the beam, to essentially zero (i.e. indistinguishable from noise fluctuations), for trajectories located very far from the incident beam (|x|>>w). The maximum pulse height depends on the beam waist, 2w, and the size of the particles, as well as in some cases the refractive indices of the particles and surrounding fluid. (This depends on the extent to which light scattering is significant relative to refraction and reflection in contributing to the overall light extinction signal.) A crucial assumption is that the particle trajectories are distributed randomly (i.e. occur with equal frequency) within the flow channel.

This assumption is usually valid, given the typical dimensions of the flow channel and the relatively low flow rates utilized. It is also assumed that the number of particles passing through the sensor is sufficiently large that the statistical fluctuations in the number of particles having trajectories with any given x-axis value (i.e. over any (narrow) range of x values) can be ignored.

The relationship between particle size and pulse height for the sensor in a focused light scattering device is therefore radically different from that obtained for a sensor of conventional design. In the latter case, irrespective of their trajectories, particles of a given size (and composition) give rise to pulses of nearly uniform height. This behavior is important for sensor design for the conventional SPOS method. The typically small variations in pulse height that occur, for example, when measuring polystyrene latex "standard" particles of essentially uniform size are caused by variations in the incident beam intensity within the OSZ along the x- and y-axes, for a given z-axis value.

These variations ultimately determine the resolution of the sensor. The resulting width of the PSD is therefore mostly a consequence of residual non-uniformity of illumination across the OSZ, rather than an actual range of particle diameters.

By contrast, there is an obvious deterioration in the particle size resolution for sensor design for focused light scattering devices. When a single particle passes through the sensor, it gives rise to a light-extinction pulse with a height, $\Delta V_{LE}$ that can vary between a given maximum value and essentially zero. Conversely, given a single detected pulse, it is impossible to determine the size of the particle that has produced it, solely from knowledge of the pulse height. For example, a particle that is relatively small, but which passes directly through the beam axis, yields the maximum pulse height possible for a particle of that size (and composition). Alternatively, a particle that is much larger but which passes relatively far from the beam axis yields a pulse height that could actually be the same, depending on its size and trajectory. Even though the large particle is able to intercept a much larger area of incident illumination than the small one, the average intensity incident on it is smaller than the intensity incident on the small particle.

Hence, the resulting pulse height could turn out to be the same as that produced by the small particle. Obviously, there are an infinite number of pairs, {d, |x|}, of particle diameters and minimum beam-trajectory distances that can give rise to the same pulse height. The particle diameter, d, and the resulting pulse height, $\Delta V_{LE}$, are effectively "decoupled" from each other. This is the problem of "trajectory ambiguity", which for more than twenty years has motivated the search for new light-scattering based schemes for particle size determination using Gaussian beams.

The effects of trajectory ambiguity described above might present a difficulty in measuring the size of a single particle, or a relatively small number of particles. However, the apparently poor size resolution associated with the sensor used for focused light scattering devices can be restored to a very acceptable level by means of appropriate mathematical deconvolution of the pulse-height data. The resulting dramatic improvement in the effective sensor resolution is possible by virtue of the fact that the sensor in a focused light scattering device is intended to be exposed to a large, statistically significant number of particles of every relevant diameter, or range of diameters, contained in the sample of interest. This is the circumstance that renders the new sensing method very useful for particle size analysis, in sharp contrast to the situation that holds for "contamination" applications. There, the sensor is exposed to relatively small numbers of particles of any given size, for which statistical significance is often not achieved.

The "raw" response of the sensor used in a focused-beam device, like its conventional SPOS predecessor, consists of the pulse height distribution (PHD)—a histogram of particle "counts" vs pulse height, $\Delta V_{LE}$. The pulse-height scale is typically divided into a relatively large number (e.g. 32, 64 or 128) of "channels," or "bins," each of which encompasses an appropriately narrow range of pulse height voltages, thus defining the voltage resolution of the PH). It is usually convenient to establish channels that are evenly spaced on a logarithmic voltage scale. Measurement of a new pulse causes the number of particle counts stored in the appropriate pulse height channel in the histogram to be incremented by one. Data are ideally collected from the particle suspension of interest for a sufficiently long time that the resulting PHD becomes statistically reliable, and thus smooth and reproducible. This means that the number, NI, of particle counts collected in the I-th pulse-height channel is statistically significant, dominating the fluctuations due to statistical "noise," for all I, e.g. for $1 \leq I \leq 128$, in the case of 128 channels. Assuming Poisson statistics, this means that NI>>NI, for all I. Relatively high levels of particle concentration are possible because the sensor responds to only a small fraction of the total number of particles passing through it. For example, concentrations in the range of hundreds of thousands of particles/ml, in sample sizes of tens of mls, can be measured. That is, millions of particles can be present, a portion of which is passed through the beam of light and counted. The fraction of particles that are actually counted, relative to the number of particles present in the sample (Np), is known as phid, or "sensor efficiency," and is calculated by taking the ratio of the particles actually detected over the number of particles in the sample. The number of particles detected over the number of particles in the sample typically ranges from about 0.5 to about 5%.

The fact that the sensor efficiency is so relatively small is not surprising. In the case of a tightly focused beam, the width, a, of the flow channel is invariably much larger than the nominal width, 2w, of the focused beam. Therefore, most of the particles passing through the sensor are exposed to negligible levels of light intensity, because their trajectories are located so relatively far from the beam axis—i.e. |x|>>w. Consequently, only a small fraction of the total number of particles is able to "block" enough light to give rise to detectable pulses, relative to the prevailing noise level. The great majority of particles pass undetected through the sensor.

While this limitation may appear to be serious, in practice it is of little concern, for two reasons. First, the fraction, phid, of particles that produce detectable, measurable pulses will be fixed for a given sensor width, a, even though the value changes with particle diameter, d. Second, the new sensing method is intended for use in determining the particle size distribution (PSD) for samples that, by definition, are highly concentrated to begin with. Even following dilution, if required, the concentration of particles of any given size (i.e. within any (narrow) size range) is, by definition, relatively high. Assuming a suitable flow rate and data collection time, the resulting PHD will possess an acceptable signal/noise ratio, with a low level of statistical fluctuations. Hence, even though only a small fraction of the available particles will contribute to the raw data, the resulting PHD will be representative of the much larger number of particles in the sample that are ignored. Therefore, a reliable and accurate PSD, representative of the entire sample, can be obtained from the "inefficient" sensor used in the focused light scattering devices described herein.

Several additional features of the PHD that can be obtained are noteworthy. First, as a consequence of the fact that the particle trajectories span a large range of |x| values, passage of uniform particles through the sensor indeed results in a PHD containing a wide range of pulse heights. In this case, these range from the threshold of individual pulse detection (dictated by the prevailing r.m.s. noise level), roughly 5 millivolts (mV), to a maximum of approximately 326 mV for the nominal "end" of the distribution. (This excludes a small number of "outlier" pulses, due to agglomerates and over-size primaries that extend to 500 mV). Given the uniformity of the particles, this 65-fold range of pulse heights can only be ascribed to differences in particle trajectory. (To a first approximation, one can neglect variations in the beam width over the depth of the flow channel, as discussed earlier.)

Second, as expected, the PHD is highly asymmetric, skewed greatly in the direction of smaller pulse heights. Clearly, there are many particle trajectories that sample a large range of |x| values (and, hence, beam intensities), but only relatively few that probe the central portion of the Gaussian profile, where the intensity is substantially uniform. The PHD exhibits a broad, smooth upswing in the number of particles with increasing pulse height, accelerating to a relatively sharp peak, followed by a dramatic decline to the baseline, representing zero pulse events. This sharp "cut-off" at the upper end of the distribution defines the maximum pulse height, referred to hereafter as $^M\Delta V_{LE}$. The counts collected at this maximum value represent particles that passed through, or very close to, the center of the beam—i.e. trajectories with x approximately equal to 0—where the fraction of total incident light flux "blocked" by the particles is the largest value possible. The counts collected in smaller pulse height channels represent particles that passed further from the beam axis; the greater parameter |x|, the smaller the resulting pulse heights.

There is a relationship between the particle trajectory and the resulting pulse height. Trajectory "A" gives rise to extinction pulses having the maximum pulse height, $^M\Delta V_{LE}$, immediately preceding the upper cut-off of the PHD. Trajectories "B," "C," "D" and "E" located progressively further from the beam axis, give rise to pulses with correspondingly lower pulse heights and progressively lower numbers of particle counts.

Eventually, the number of particle counts per channel approaches zero, as the pulse height reaches the detection limit (approximately equal to 5 mV). The reproducibility of the PHD depends only on the degree to which the number of counts contained in the various channels is large compared to statistical fluctuations.

Therefore, the "reliability" (i.e. the smoothness and reproducibility) of the PHD should depend on the total number of particles counted during a measurement. For a given particle size there will obviously exist a minimum number of pulses that should be counted and analyzed, below which the PHD should be expected to exhibit significant, irreproducible "structure" from one measurement to the next, due to statistical noise.

Again, the PHDs produced by the new sensor have meaning only to the extent that relatively large, statistically meaningful numbers of particles of the same size are detected during the data collection period. Only if this is true can one expect to obtain optimal, reproducible PHD results, and correspondingly accurate, representative particle size distribution (PSD) results derived from the latter using the methods discussed below.

To confirm that the data measured is significant, one can overlay two or more PHDs taken from measuring the same sample in multiple runs.

Exposing the sensor to larger particles will yield a PHD that is shifted to larger pulse heights. Specifically, the maximum pulse height, $^M\Delta V_{LE}$, corresponding to particle trajectories passing through, or very close to, the beam axis, increases.

An LS-type sensor can be used in place of, or in addition to, an LE sensor. The LS-type sensor uses a light collection means—typically one or more lenses—in order to gather scattered light rays originating from individual particles passing through the OSZ, created by the incident light beam.

The lens system is designed to collect scattered light over a particular, optimal range of angles, typically encompassing relatively small angles of scattering. In the scheme shown in FIG. 2, a mask 50 has been placed in front of the first collection lens. Mask 50 comprises an outer opaque ring 52 and an inner opaque area 54, which form a transparent ring 56. Mask 50 allows only light rays with scattering angles, theta, located within an imaginary annular cone defined by angles theta1 and theta2 (i.e. theta1≤theta2) to impinge on the first collection lens 62. Typically, this lens is centered on the axis of the incident beam, at an appropriate distance (i.e. its focal length) from the center of the flow channel, causing a portion of the diverging scattered light rays from the OSZ to be captured by the lens and become approximately collimated. A second lens 64 can then be used to focus the resulting parallel scattered rays onto a suitable (small-area) detector $D_{LS}$. The resulting signal is "conditioned" by one or more electronic circuits, typically including the functions of current-to-voltage conversion and amplification. There is a crucial difference between the signal, $V_{LS}$, created by this optical scheme and the signal, $V_{LE}$, produced by the LE-type sensor. Unlike the latter, the LS-type sensor, by design, prevents the incident light beam emerging from the back window of the flow cell from reaching the detector, $D_{LS}$. Instead, the incident beam is either "trapped" by means of a suitable small opaque beam "stop" (e.g., the inner opaque area 54) or deflected by a small mirror away from the lens that is used to collect the scattered light rays originating from the OSZ. Consequently, the relatively large "baseline" level, $V_0$, necessarily present in the overall signal, $V_{LE}$, produced by the LE-type sensor is now absent from the LS signal, $V_{LS}$. Ideally, the new "baseline" signal level is zero—i.e. there should be no scattered light generated from sources within the OSZ in the absence of a particle. In practice, of course, there will be some amount of background light caused by light scattered from the surfaces of the front and/or back windows of the flow channel, due to imperfections on, or contaminants attached to, the latter surfaces. In addition, there may be fluctuating background light due to scattering from small contaminant particles suspended in the diluent fluid. Also, for some samples there may be fluctuations in background light produced by a "sea" of ultra-fine particles which comprise a major fraction of the overall particle population, but which are too small to be detected individually.

When a particle of sufficient size passes through the OSZ, defined by the incident Gaussian light beam and front and back windows of flow channel, a momentary pulse occurs in the output signal produced by the detector, $D_{LS}$, and associated signal conditioning circuit. In general, one might naively expect that the larger the particle, the greater the amount of light scattered by it, assuming the same trajectory, and therefore the greater the height of the signal pulse.

In practice, the actual pulse height depends not only on the size of the particle, but also its composition—specifically, its index of refraction (and that of the surrounding fluid) and absorbance, if any, at the incident wavelength. The pulse height also depends on the wavelength of the beam and the orientation of the particle as it passes through the OSZ, if it is not spherical and homogeneous Finally, for particles comparable in size to, or larger than, the wavelength, the scattering intensity varies significantly with the scattering angle. Consequently, in this case the pulse height depends on the range of angles over which the scattered light is collected and measured.

The relationship between the scattered light "radiation pattern" (i.e. intensity vs angle) and all of these variables is described by classical Mie scattering theory, which takes into account the mutual interference of the scattered light waves within the particle.

In general, the larger the particle, the more complex (i.e. non-isotropic) the angular dependence of the scattered intensity resulting from intra-particle interference. In order to optimize the response and performance of the LS-type sensor, one must confine the collection of scattered light to a range of angles, theta, for which the net integrated response, $\Delta V_{LE}$, increases monotonically with the diameter, d, of particles of a given composition (i.e. refractive index) over the largest possible, or expected, size range. This requirement can usually be satisfied by choosing a range of relatively small angles, theta1<theta<theta2, close to the forward direction. In this way, one avoids "reversals" in the integrated scattering intensity with increasing particle size due to variations of the intensity with changes in angle, especially significant at larger angles as a consequence of Mie intra-particle interference.

There are two properties of the signal, $V_{LS}$, produced by the new LS-type sensor that are qualitatively different from the properties of the signal, $V_{LE}$, produced by the corresponding LE-type sensor. First, the signal pulse caused by passage of a particle through the OSZ and the "overall" signal, $V_{LS}$, are essentially the same in the case of the LS-type sensor. The relatively high background signal level that accompanies the pulse of interest in the LE-type sensor is absent: (The same situation clearly holds for a conventional LS-type sensor).

Therefore, in the case of relatively small particles that give rise to pulses of low magnitude, the signal/noise ratio achieved in practice using the LS method should be significantly better than that realized using the LE method. This advantage becomes more important the smaller the particle and the weaker the resulting pulse, as the latter approaches the prevailing noise fluctuations. Another way of appreciating the inherent advantage of the LS method over its LE counterpart is to realize that the former is based on "detection at null." That is, quantitative detection of a pulse ideally is carried out in the presence of zero background signal. From a signal/noise perspective, this is in sharp contrast to the situation that obtains for the LE method, which requires high "common mode rejection." The "common-mode" signal, $V_0$, is always present in the raw signal, $V_{LE}$, and must be subtracted, or otherwise suppressed, in order to extract the (often small) signal pulse of interest.

There is a second important and distinguishing property of the LS signal, $V_{LS}$. The signal/noise ratio associated with the measurement of $\Delta V_{LS}$ can in principle be improved by increasing the power of the incident light beam, so as to increase the light intensity incident on a particle at all points within the OSZ. Therefore, in principle one can reduce the lower size detection limit for the new LS sensor by increasing the power of the light source, as for a conventional LS sensor. Eventually, a lowest size limit will be reached, based on noise fluctuations associated with the suspending fluid and/or the light source and detection system. Of course, as discussed above, the lower particle size limit can also be improved for the new LS-type sensor by reducing the width, 2w, of the incident beam, assuming no change in the power of the latter. This action will obviously increase the maximum intensity incident on the particles that pass through the beam axis (x=0), and therefore the height of the largest resulting pulse for a particle of given size, as well. However, this method of improving the sensitivity eventually reaches a point of diminishing return, due to limitations imposed by diffraction theory (establishing a minimum beam width) and excessive variation of the focused beam width over the depth, b, of the flow cell due to excessively-long depth of field. By contrast, an increase in the power of the light source has relatively little effect on the lowest particle size that can be measured using the LE method. For example, a doubling of the power of the light source will result in a doubling of the baseline signal level (FIG. 2), to 2V0. The height of the pulse, $\Delta V_{LE}$, produced by a particle of the same size and trajectory will also be doubled, assuming no change in the beam width.

However, the root-mean-square magnitude of the noise fluctuations associated with the relatively high baseline signal level will typically also be approximately doubled, because these fluctuations are usually associated with the light source and therefore scale with the output power. Hence, one expects little or no improvement in the signal/noise level for the LE-type sensor. Consequently, there should be little or no reduction in the lower size detection limit achievable by the LE method as a consequence of increasing the power of the light source. An improvement will be realized only if the signal/noise ratio associated with the light source improves with increased power.

When uniform size particles flow through the new LS-type sensor, depending on their trajectories they are individually exposed to different values of maximum incident intensity, given by Equation 7, with r=x, z=0. (For simplicity, it can be assumed that the particles are much smaller than the beam width, so that every point in a given particle is exposed to the same intensity at any given time.) Therefore, as with the new LE-type sensor, the height, $\Delta V_{LS}$, of the resulting pulse generated by a particle of given size depends on the distance, |x|, of closest approach (z=0) to the axis of the incident beam. The smaller the distance |x|, the larger the value of $\Delta V_{LS}$.

Hence, like its LE counterpart, the LS-type sensor generates a distribution of widely varying pulse heights, $\Delta V_{LS}$, when a suspension of uniform particles passes through it at an appropriate flow rate. The shape of the resulting PHD bears a strong qualitative resemblance to the highly asymmetric shape of the PHDs obtained using the new LE method, exemplified in FIGS. 4, 6 and 7. That is, the number of pulse counts (y-axis) is relatively small at the smallest measurable pulse height just above the noise fluctuations) and rises with increasing pulse height, $\Delta V_{LS}$. The pulse count value culminates in a peak value at a maximum pulse height, referred to as $^M\Delta V_{LS}$, corresponding to particle trajectories for which |x|≈0. Above $A\Delta V_{LS}$ the number of pulse counts ideally falls to zero, assuming that the particle concentration is below the coincidence concentration (discussed earlier) for particles of that size, so that at most one particle effectively occupies the OSZ at any given time. Of course, a PHD obtained using the new LS method usually pertains to particles that are smaller—often significantly so—than those used to generate a typical PHD using the new LE method.

As noted above, the shape of the PHD—number of pulse counts vs $\Delta V_{LS}$—generated for uniform particles using the new LS method is qualitatively similar to the shape of the PHD obtained for uniform (typically larger) particles using the new LE method. Both kinds of PHDs share the distinguishing characteristic of a sharp "cut-off" following their respective peak number of pulse counts, coinciding with their maximum pulse height values, $^M\Delta V_{LS}$ and $^M\Delta V_{LE}$. However, it should be appreciated that there are quantitative differences in the shapes of the two kinds of d=1, notwithstanding their qualitative similarities, even for the same particle size—e.g. d=1 μm. The "front end" design of the new LS-type sensor— i.e. the focused light beam and relatively thin flow cell—is essentially the same as that utilized for the new LE-type sensor. Therefore, what distinguishes one type of sensor from the other concerns the means and manner of light detection and the type and magnitude of the response pulses generated by each method, even in the case of particles of the same size. For the new LS method, the response is due only to light scattering, and its magnitude, $\Delta V_{LS}$, is proportional to the intensity of the light incident on the particle, all other relevant variables being the same.

By contrast, for the new LE method the magnitude of the response, $\Delta V_{LE}$, is a more complex function of the intensity incident on the particle. First, the response is due to a combination of physical effects—refraction (and reflection) plus light scattering. However, the scattering phenomenon asserts itself in an "inverse" sense. That is, a small fraction of the incident light flux is removed from the beam before it reaches the detector.

Second, over the typical size range for which the new LE method is applicable, there is a substantial variation in the incident intensity across the particle. Therefore, it should not be surprising that the fractional change of pulse height due to a given change in |x|, dependent on both particle size and trajectory, is generally different for the two methods. Similarly, the fractional change in pulse height with particle diameter, dependent on both particle size and trajectory, is also generally different for the two methods.

The task of converting the "raw" data—the PHD—obtained from a sample of suspended particles into the object ultimately desired—the particle size distribution, or PSD, is described in detail below.

It is useful to compare this task conceptually with the operation required in the case of a conventional LE- or LS-type sensor. There, the height of the pulse due to passage of a particle through the OSZ is nearly independent of its trajectory, because the intensity of the incident beam is designed to be approximately constant across the flow channel (i.e. along the x-axis) for a given z-axis value (e.g. z=0). Consequently, particles of a given size ideally give rise to pulses of substantially the same height, and the resulting PHD is therefore, in effect, equivalent to the final desired PSD. There is a one-to-one correspondence between a given, measured pulse height, $\Delta V_{LE}$ (or $\Delta V_{LS}$), and the particle diameter, d. If particles of a larger or smaller size pass through the sensor, the resulting pulse heights are larger or smaller, respectively. A "calibration curve," consisting of pulse height vs particle diameter, is all that is needed to obtain, by simple interpolation, the PSD from the PHD. Obtaining the raw PHD data using the conventional SPOS method is equivalent to determining the final, desired PSD.

By contrast, as discussed earlier, the response of the LE- (or LS-) type sensor is much more "convoluted." Even in the simplest case of particles of a single size, the resulting PHD consists of a broad spectrum of pulse heights, from the smallest values just above the prevailing noise fluctuations, to the maximum value, $^M\Delta V_{LE}$ (or $^M\Delta V_{LS}$), associated with that size. Therefore, in the typical case of particles of widely varying size, the resulting PHD consists of an even wider assortment of pulse heights. No longer is there a simple correspondence between pulse height and particle size. It is therefore no longer a simple, straightforward procedure to transform the set of particle counts vs pulse-height values contained in the PHD into the desired size distribution—particle counts vs particle diameter.

It typically involves three procedures to convert the PHD to the desired PSD. First, the raw PHD must be inverted, or deconvoluted, using a specialized mathematical algorithm. Its purpose is to convert the "wide-spectrum" PHD produced by the new LE- (or LS-) type sensor into a "sharp", idealized PHD, equivalent, in effect, to what would have been obtained using a conventional LE- (or LS-) type sensor. Such an idealized, deconvoluted PHD—hereinafter referred to as the dPHD—has the property that all pulses of a given height, $\Delta V_{LE}$ (or $\Delta V_{LS}$), belong exclusively to particles of a given size (assuming, always, particles of a given composition). The dPHD is equivalent to what would have been obtained if all of the particles contributing to the original PHD had passed through the center (axis) of the incident beam. A second straightforward procedure is then carried out. A preliminary, or "raw", PSD is obtained from the dPHD by simple interpolation of the calibration curve that applies to the specific new LE- (or LS-) type sensor utilized—e.g. the curve shown in FIG. 8A. This procedure permits a one-to-one translation of each deconvoluted pulse height value in the dPHD into a unique particle diameter associated with this value, thus yielding the raw PSD. A third procedure is then needed to convert the raw PSD thus obtained into a final PSD that is quantitatively accurate. The number of particle counts in each diameter channel of the raw PSD is the number of this size that actually contributed to the measured PHD. As discussed above, this is typically only a small fraction of the total number of particles of the same size (i.e. within the size range defined by the diameter channel) residing in the volume of sample suspension that passed through the sensor during data collection. This fraction, phid, of particles actually detected by the new LE- (or LS-) type sensor varies significantly with the particle diameter, d. The third procedure involves multiplying the number of particles contained in each diameter channel of the raw PSD by the value of 1/phi1 that applies for that channel.

This operation yields the final, desired PSD, describing the number of particles of each size estimated to reside in the quantity of sample suspension that passed through the sensor during data acquisition. Values of 1/phid for each value of diameter, d, can be obtained from the sensor efficiency curve, phid vs d, by interpolation.

There are two independent algorithms presented herein for deconvoluting a measured PHD, to obtain the dPHD, hereinafter referred to as "matrix inversion" and "successive subtraction." Implementation of either procedure is based on the property that the response of the new LE- (or LS-) type sensor—like its conventional SPOS counterpart—is additive. Because the particles passing through the sensor give rise to signal pulses one at a time, the resulting PHD can be considered to be composed of a linear combination, or weighted sum, of individual PHDs corresponding to uniform particles of various sizes, referred to as "basis vectors." (This term is well known in linear algebra.) Each of these basis vectors represents the response of the system to a statistically significant number of particles of a single, given size.

In one embodiment, the focused light scattering device described herein incorporates both the new LE- and LS-type SPOS sensors in a single sensor, having two independent output signals, $V_{LE}$ and $V_{LS}$. The resulting dual "LE+LS" design offers increased capability and flexibility, providing single-particle counting and sizing over a relatively large range of particle sizes. The LS-type sensor subsystem can be used to extend the size range below the lower detection limit provided by the new LE-type sensor subsystem. The extent to which the lower particle size limit can be extended depends on a variety of parameters. These include: the width, 2w, of the narrow (typically focused) beam within the measurement flow cell; the power of the light source; the range of angles over which scattered light is collected for implementation of the new LS-type sensing function; and the physical properties, including the refractive index, of both the particles and the suspending fluid.

The dual LE+LS sensor includes a light source, preferably consisting of a laser diode module, typically having an output wavelength in the range of 600 to 1100 nanometers (nm). The beam produced by the light source means preferably is collimated (parallel) and "circularized"—i.e. the intensity is a function only of the distance, r, from the central axis. Furthermore, the beam preferably has a Gaussian intensity profile, along any axis normal to the axis of propagation of the beam. The new LE+LS sensor also includes a focusing means, typically a single- or multi-element lens, capable of focusing the starting collimated light beam to the desired beam width, 2w, at the center of the measurement flow channel in the OSZ, consistent with the desired particle size range.

It is assumed that the focusing means has an appropriate focal length, thus yielding acceptable values for both the width and depth of field of the focused beam. The latter is preferably significantly longer than the thickness, b, of the flow channel, in order to optimize the resolution of the resulting PSD.

A measurement flow cell is typically fabricated from a suitable transparent material, such as glass, quartz or sapphire, or alternative semi-transparent material, such as PTFE (e.g. Teflon™, manufactured by DuPont) or other suitable plastic that is sufficiently transparent at the operating wavelength and compatible with the fluid-particle mixture. A suitable fluidics system, including a flow pump means and optional means for automatic dilution of the starting sample suspension (if needed), are typically required to facilitate the steady flow of the particle-fluid suspension through the flow cell. The flow rate, F, is usually chosen to be the same as, or close to, the value used to generate the calibration curve for the LE- or LS-type sensor.

The thickness, b, of the flow channel should be small enough to achieve a high coincidence concentration limit and as uniform a beam width as possible (ideally with b<<depth of field), resulting in improved resolution for the final PSD. However, it must be large enough to prevent frequent clogging by over-size particles (e.g. agglomerated primaries and contaminants in the fluid/diluent). The width, a, of the flow channel is also chosen to strike a compromise between two competing effects. A relatively large value reduces the impedance to the flowing fluid-particle mixture and lowers the velocity (and increases the pulse width) for a given flow rate, F. However, the larger parameter a, the smaller the sensor efficiency, phid, for any given particle diameter, d. This results in a smaller fraction of particles in the sample actually contributing to the measured PHD and final PSD, which, if too small, may be undesirable. The new LE+LS sensor contains two separate light collection and detection subsystems, used independently to extract the desired LE- and LS-type signals. The LE-type signal can be captured using a small light reflecting means M (e.g. mirror), positioned so as to intercept the narrow beam of incident light after it passes through the flow cell and fluid-particle mixture. The resulting transmitted beam, thus deflected away from the optical axis of the combined sensor, is caused to impinge on a nearby light detection means $D_{LE}$. The latter typically consists of a small-area, solid-state (silicon) detector, operating in a linear region and having a spectral response that is matched to the wavelength of the light source, thus providing an output signal with an acceptable signal/noise (S/N) ratio. The output of the detector means is typically a current (the "photocurrent"), which can be conditioned by a current-to-voltage converter ("transimpedance" amplifier), yielding an output signal in the generally desired form of a time-varying voltage, $V_{LE}(t)$.

Alternatively, a small detector element can be placed directly in the path of the light beam after it emerges from the flow cell, thus eliminating the need for the intermediate light reflecting means discussed above. Regardless of whether a mirror or detector element is used to "capture" the transmitted light beam, there are two requirements. First, the means used must function as an effective beam "stop." That is, it must be able to prevent any significant fraction of the arriving light flux from being reflected back toward the flow cell, thus becoming a source of "stray" light. Through unintended internal reflections from the various optical surfaces, a portion of the stray light can find its way to the scattering detection means $D_{LS}$, thus corrupting the resulting LS signal, by contributing a portion of the incident intensity to the latter.

Second, the means used to capture the LE signal must be small enough not to intercept, and therefore block, scattered light rays at any angles that are intended to be captured and redirected to the light detection means $D_{LS}$, as discussed below. Separately, scattered light originating from particles passing through the OSZ is collected over a range of scattering angles, theta, with theta1<theta<theta2, where angles theta1 and theta2 are defined by a suitable aperture means, such as an annular mask fabricated from a photographic negative with an outer opaque portion, a transparent intermediate portion, and an inner opaque portion. The scattered rays selected by the mask are allowed to impinge on a collecting lens of appropriate focal length and location, which converts the diverging scattered rays into an approximately parallel beam. A second lens is then typically used to refocus the rays onto a relatively small light detection means $D_{LS}$. As in the case of the LE subsystem, the output signal of $D_{LS}$ is typically a current, which can be optionally conditioned, typically by means of a transimpedance amplifier, so that the final output is in the form of a time-varying voltage, $V_{LS}(t)$.

The signals $V_{LE}(t)$ and $V_{LS}(t)$ can be organized into respective pulse height distributions PHD by pulse height analyzers. The PHDs are then respectively deconvoluted in computer deconvolution means, which ultimately compute a pair of respective particle size distributions ("PSD").

This embodiment can be implemented as an LE-type or LS-type sensor only, simply by removing (or not installing in the first place) the optical elements, detection means and signal conditioning circuitry associated with the unwanted subsystem. In this case, it may be useful to adjust the width, 2w, of the focused beam within the measurement flow channel, in order to optimize the resulting performance of the LE- or LS-type sensor. This parameter will impact the usable particle size range, coincidence concentration limit and minimum detectable particle size differently for the two sensing modes, as discussed earlier.

Hydrodynamic Sample Injection

In one embodiment, the apparatus uses hydrodynamic sample injection, such as is described in Pelssers et al., Journal of Colloid and Interface Science, Volume 137, Issue 2, July 1990, Pages 350-361. Colloidal dispersions of platelets in serum or other media, can be hydrodynamically focused into a narrow stream, with widths ranging from about 3 to about 10, preferably about μm width.

The use of a focused light scattering technique allows one to measure relatively small particle sizes. However, where a focused beam hits particles in a relatively wide sample stream (as described above, where the beam is narrower than the measurement flow channel in the width direction), the detection method relies somewhat on statistics. That is, where the beam is substantially narrower than the sample stream, an assumption is made that there is an equal distribution of particles in the sample stream, so that one can extrapolate the results of the interaction of the light in the narrow beam with the particles in its path over the entire width of the sample stream. By hydrodynamically focusing the sample into a stream with a relatively narrow width, and using a focused light source, it is possible to count all or most of the particles in the sample stream, and rely to a lesser extent on statistics.

Figure 3:
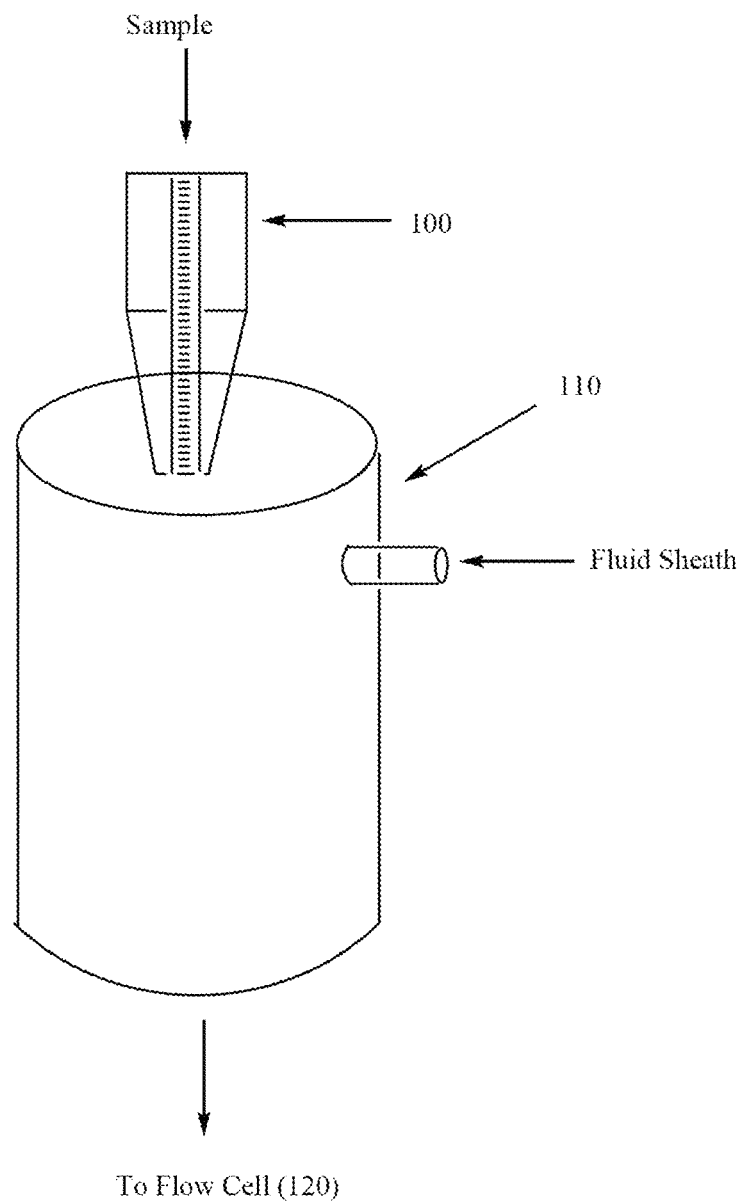
FIG. 3 is a schematic illustration of a hydrodynamic flow injector.

A representative injector for carrying out hydrodynamic injection is shown in more detail in FIG. 3. As shown in FIG. 3, As shown in FIG. 3, a sample passes through an inlet port (100), through a fluid sheath (110), and outward through the bottom of the injector into a flow cell (120). The sample travels through the sample injection tube, with fluid from a fluid sheath surrounding the stream, and hydrodynamic focusing within the flow cell forcing particles into a single-particle-file stream where laser light intercepts the stream at a sample interrogation point. The design of the flow cell, when a hydrodynamic injector is used, permits particles to flow through the center of the flow cell. Increasing the sample pressure increases the core diameter and the flow rate.

Mechanical Shearing Devices (For EQELS and/or ISADE Devices)

Certain biological and non-biological species require mechanical shear for activation. Species may be a cell, a protein, ribo- or deoxyribonucleic acid, polysaccharides, aggregated cells or molecules or the like. Representative examples of cells include, but are not limited to, endothelial cells and platelets, and representative examples of molecules include von Willebrand factor and DNA. Both biological and non-biological species may aggregate to exhibit an effect on the mechanical properties of a fluid. Examples include thixotropy (shear thinning) and rheopexy (shear thickening). Biological cells, molecules like fibrin, vWF, tubulin, myosin, and the like, and non-biological materials, like paints or inks, are examples.

Figure 4:
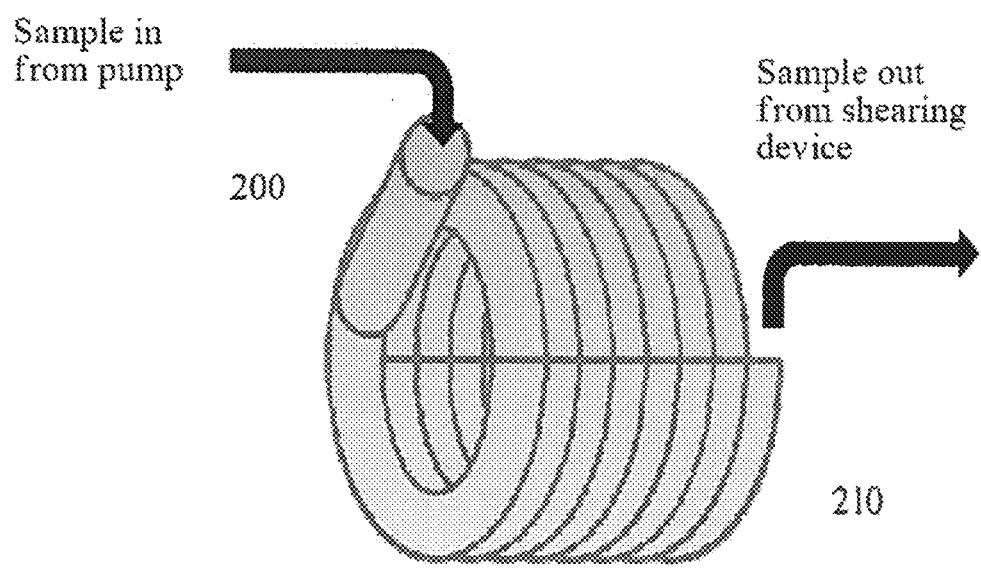
FIG. 4 is a schematic illustration of a device to apply precise mechanical shear to a sample.

The provision of mechanical shear can be accomplished by integrating a mechanical shearing device into the apparatus described herein. Although there are many means for introducing mechanical shear, any one of which can be used, in one embodiment, a suitable device is shown in FIG. 4. In this device, a sample is placed in a suitable container. The sample in the container may then be extricated from the container manually, or by a robotic and then introduced into a pump. In one aspect of this embodiment, the pump is a precision pump that can produce a precise and continuous flow rate of the sample within the shearing device (200). The shearing device (200) is composed of a hollow fiber that may be linear or coiled, though in the embodiment shown in FIG. 4, it is coiled. In one aspect of this embodiment, the hollow fiber is composed of materials that minimize interaction with the sample or under certain other cases or circumstances may interact with the sample in a specific manner. For example, the inner surface of the hollow fiber may be coated with collagen that interacts with vWF or with platelets. The length of the hollow fiber and the inter diameter of the hollow fiber can be precisely known. Further, the pressure drop across the fiber can be precisely known, from the flow rates, volume flux, and/or from pressure sensors located at each end of the hollow fiber. From these data, the mechanical shear rate experienced by the sample can be calculated. The effluent sample can then be passed on to the scattering chamber of EQELS or the hydrodynamic injector of the ISADE device described herein by means of a linking hollow fiber. In this manner, the entire system is closed, and the sample can pass in a continuous manner from the original sample container though the shearing device and into the respective scattering chambers or hydrodynamic injector, then into an effluent chamber via an exit port (210).

Figure 5:
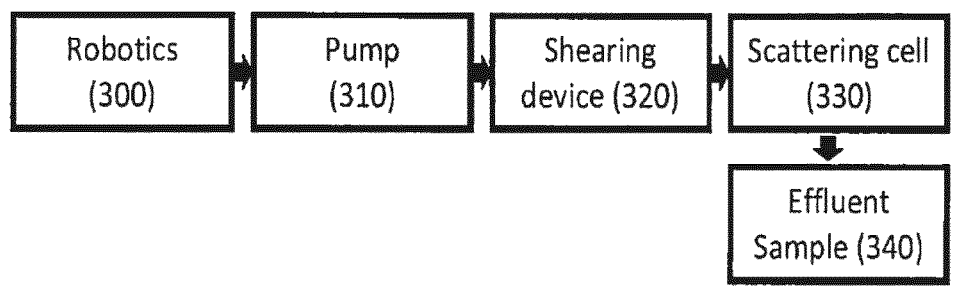
FIG. 5 is a flow chart showing the path of a fluid sample from a pump controlled by robotics, through a shearing device, to a scattering cell, where dynamic light scattering or electrophoretic light scattering can be measured, as well as microparticle detection, sizing, counting and phenotyping to where the sample leaves the device as effluent.

In use, the sample follows a path from a storage device, via a pump (310) controlled by robotics (300) through a shearing device (320), into a cell where scattered light can be detected (330), and then to an effluent container (340). Although a scattering chamber of an EQELS device is shown in FIG. 5, when the shearing device is used in connection with the hydrodynamic injector of an ISADE device as described herein, the hydrodynamic injector can substitute for the scattering chamber shown in FIG. 5.

In an alternative embodiment, shear can be provided using ultrasound; vibration; radiowaves; cone-plate, parallel plate or coutte shearing surfaces; a coaxial plunger device and the like).

II. Detection of Microparticles Ejected from Platelets

Particle shedding results from the interaction of (unprotected) cell surface P2Y12 receptors with a P2Y12 agonist, such as ADP. The ejected (shed) microparticles (MPs) have a particle size in the range of between about 0.1 and 0.6 µm, and can be observed using the methods described herein. Using the techniques described herein, microparticles ejected from platelets following interaction with a P2Y12 agonist such as adenosine diphosphate (ADP) are detected, and the detection of these MPs allows one to determine whether or not a particular P2Y12 antagonist therapy is beneficial to a patient, that is, whether the antiplatelet drug the patient is ingesting is providing adequate platelet inhibition to prevent thrombosis.

A blood sample is obtained from a patient, and, optionally, subjected to centrifugation or other purification technique known to those of skill in the art to provide a platelet-rich sample. Before the blood sample is obtained, the patient is ideally identified as someone at risk of thrombosis and the concomitant risk of strokes, myocardial infarction, and the like. The patient is being screened for his or her ability to benefit from a particular P2Y12 antagonist therapy. Some of these therapeutic agents are administered as pro-drugs, and the active metabolite is formed in vivo, and the test can determine whether the patient has the correct genetic makeup to produce the metabolite.

However, to make this determination, the drug will have to be administered to the patient in advance of the sample being obtained. How much drug, and how long in advance, depend on the particular agent being evaluated, and the selection of drug type, quantity, and advance time before testing are well known to those of skill in the art. For example, for Plavix®, a loading dose of 300-600 mg can be administered two to five hours before the screen. Alternatively, the patient can be given a normal dosage of the agent for a predetermined period of time that is sufficient to have produced the prodrug at sufficient levels to have protected the platelets (by irreversibly binding the active metabolite to the platelets).

As the sample will likely include microparticles, the sample is subjected to analysis using the single particle optical sensing device, and the number, and, optionally, size, of microparticles is counted. Then, a suitable P2Y12 agonist, such as ADP, is added, and allowed sufficient time to interact with any platelets not already bound to the P2Y12 antagonist. The sample is then passed through the sensing device again, and the number of ejected microparticles is measured.

When the number of microparticles is roughly the same before and after exposure to the P2Y12 agonist, the patient will likely respond positively to this particular P2Y12 antagonist therapy.

When the number of microparticles is significantly higher after exposure to the P2Y12 agonist, the patient will not likely respond positively to this particular P2Y12 antagonist therapy. However, the patient can be subjected to higher doses of the P2Y12 antagonist, and re-screened until a suitable dose is identified. If a suitable higher dose is not identified, a different P2Y12 antagonist can be screened, though, in one embodiment, the different P2Y12 antagonist is screened in the absence of performing additional dosing studies using the first P2Y12 antagonist.

One benefit of this screen, over pharmacogenomic screens, is that the test is rapid and inexpensive. Another benefit is that the screen assesses the function of the intact cell, whereas genetics merely looks at an individual allele. A limitation with only determining the presence of a loss-of-function allele is that there may be a gain-of function allele in a co-lateral metabolic pathway that compensates or over—compensates for the loss-of-function allele. In contrast, the instant screen looks at total cell function.

By looking at the total cell function, this screen can identify patients who can produce the active metabolite of the P2Y12 antagonist prodrug, but who have a mutation in their platelet P2Y12 receptors, such that the active metabolite does not bind effectively.

The ISADe device described above can be used to identify particles in the given size range (i.e., the size of the ejected (shed) microparticles and the size of the platelets).

Figure 6:
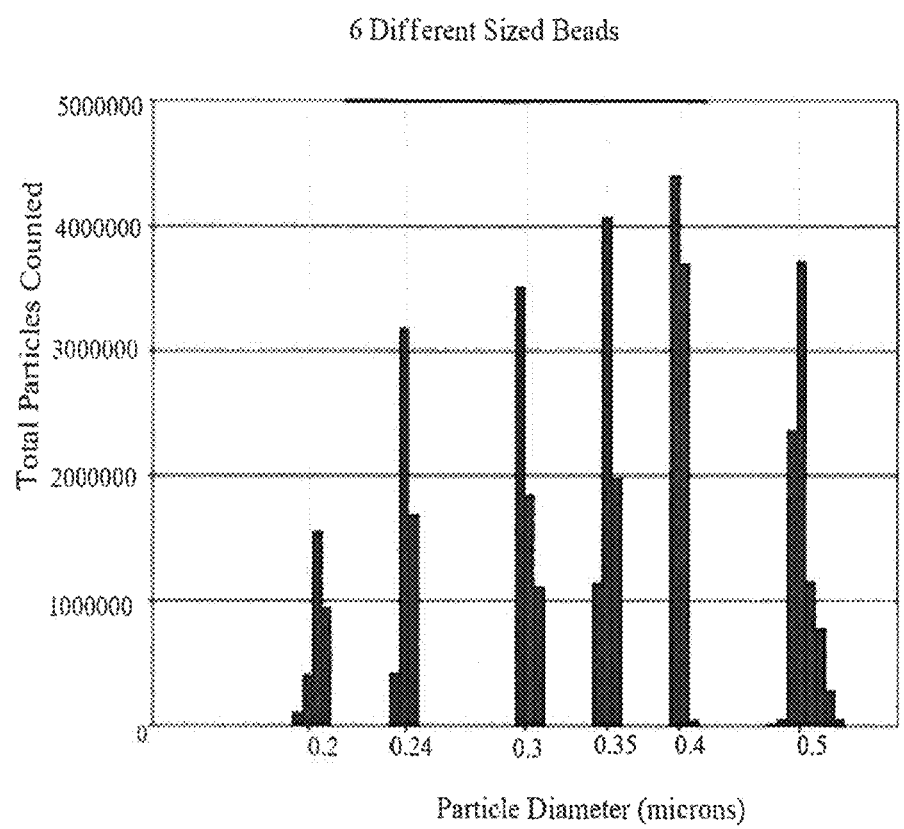
FIG. 6 is a chart showing the measurement of particles in a sample composed of 6 differently-sized polystyrene beads, assessed using the surface antigen detection enumerator light scattering device in terms of particle count (number) by particle size (μm). The chart shows the remarkable resolution of very small particle sizes. Current flow cytometers are not capable of resolution to this degree.

As shown in FIG. 6, a sample composed of 6 differently-sized polystyrene beads was introduced to the device, and assessed using the device in terms of particle count (number) by particle size (μm). The chart shows the remarkable resolution of very small particle sizes. Current flow cytometers are not capable of resolution to this degree.

Figure 7:
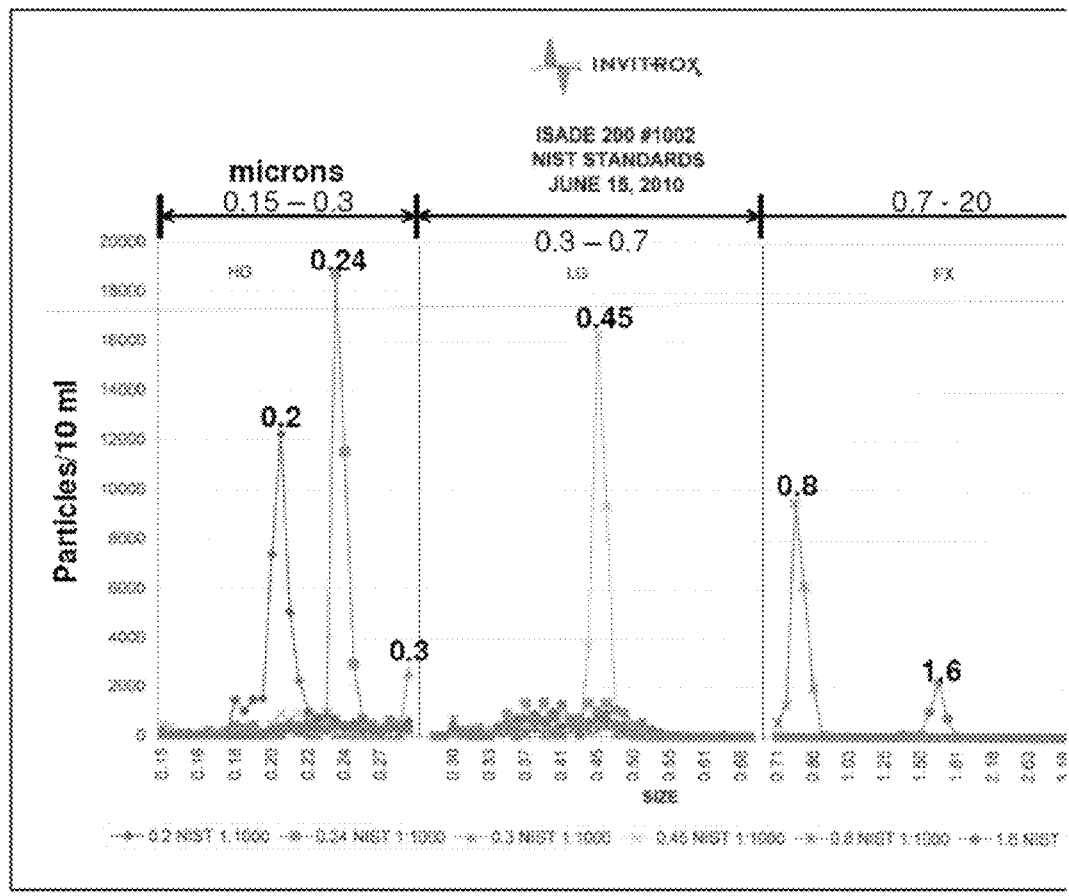
FIG. 7 is a chart showing similar data from the data shown in FIG. 4. The data in FIG. 7 is presented as points rather than as histograms, and is reflected in particles per 10 ml sample, versus particle size (μm). Also, FIG. 7 separates the size distribution into 3 different windows. In this embodiment, each window has a separate detector that has been adjusted to detect particles in a specific size range. The smallest particles are assessed from scatted light focused onto a high-gain detector, the middle window from scattered light focused onto a low gain detector, and the window with the largest particles by a light extinction method.

FIG. 7 is a chart showing similar data from the data shown in FIG. 6. The data in FIG. 7 is presented as points rather than as histograms, and is reflected in particles per 10 ml sample, versus particle size (μm). Also, FIG. 6 separates the size distribution is separated into 3 different windows. In this embodiment, each window has a separate detector that has been adjusted to detect particles in a specific size range. The smallest particles are assessed from scatted light focused onto a high-gain detector, the middle window from scattered light focused onto a low gain detector, and the window with the largest particles by a light extinction method.

Figure 8:
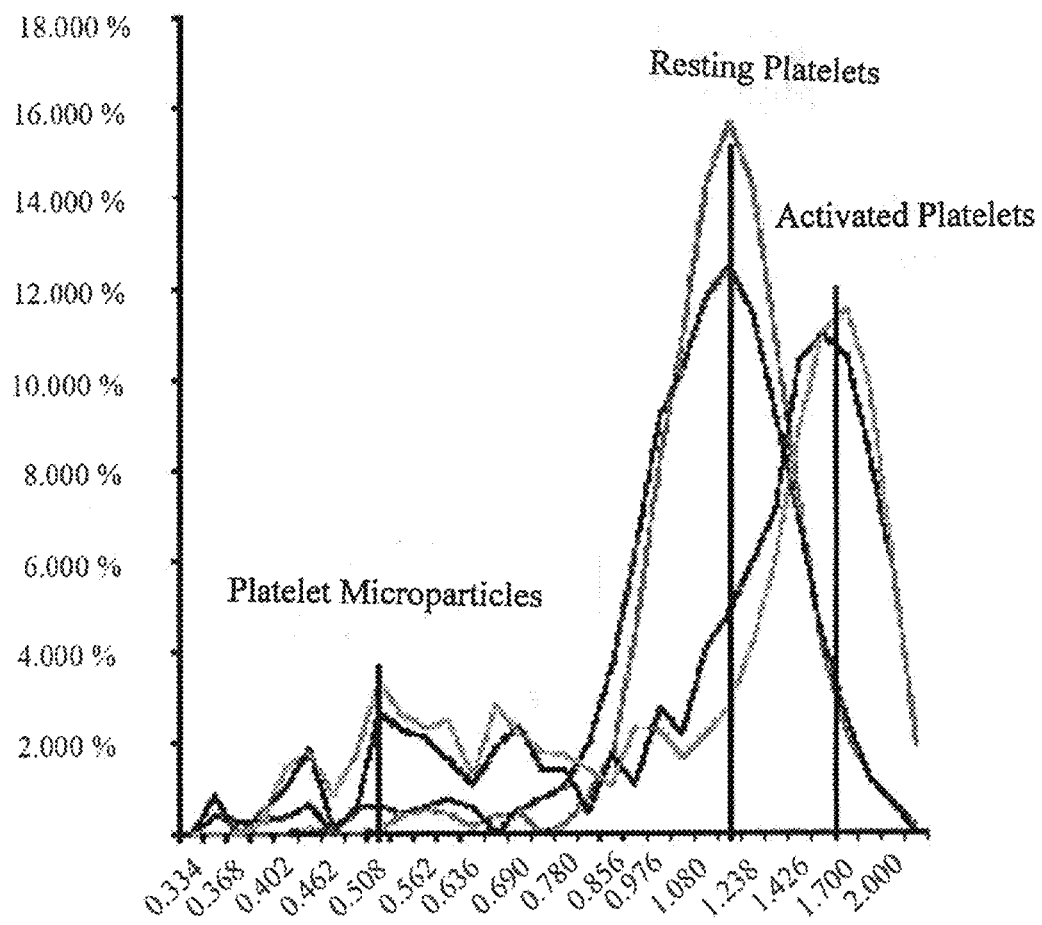
FIG. 8 is a chart showing the result of the activation of platelets using thrombin receptor activating peptide (TRAP), where platelets are enlarged when activated, and also give off microparticles (MPs).

FIG. 8 shows an example of the size distribution of normal resting human platelets, and the effect of activating the platelets with Thrombin Receptor Activation Peptide (TRAP). It is relevant to note the small number on microparticles (MP's) formed, and the increased size of the activated platelets compared to the resting platelets.

Figure 9:
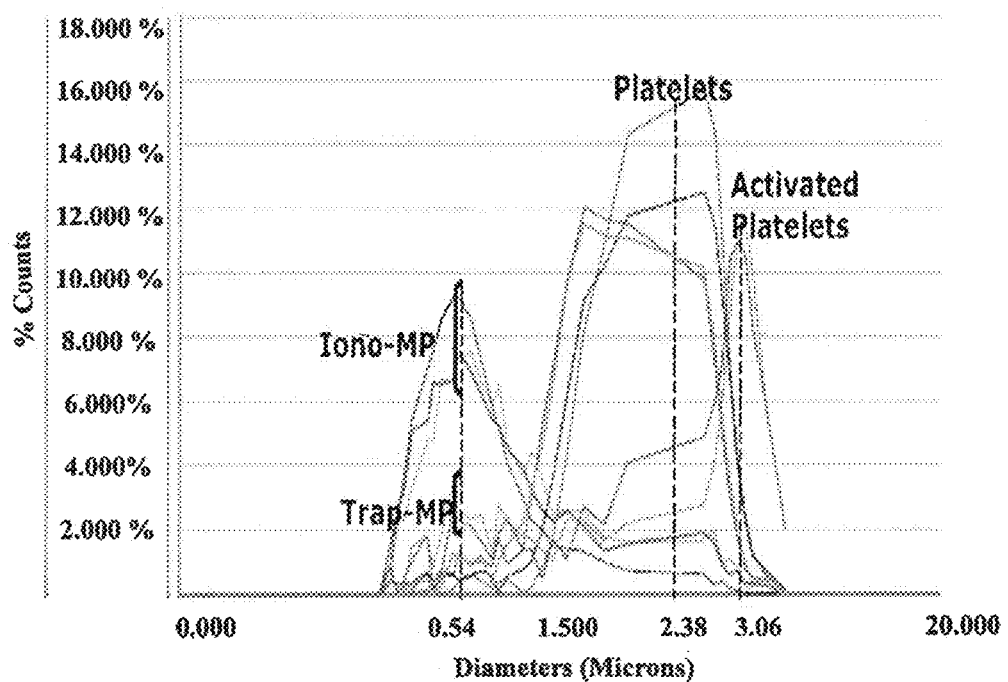
FIG. 9 is a chart showing the result of the activation of platelets using a calcium ionophore, which destroys platelets, and also causes the platelets to give off microparticles (MPs). Treated and untreated platelet size distributions are shown. What is observed is as the number of platelets decreases, the number of MPs increases.

FIG. 9 shows three different experiments, including an overlay of the results of the experiment shown in FIG. 6 with a sample where the platelets were activated with calcium ionophore. The ionophore basically destroys the platelet to produce many more MPs. Treated and untreated platelet size distributions are shown. What is observed is as the number of platelets decreases, the number of MPs increases.

In the instant assay, rather than destroying the platelets, the addition of a P2Y12 agonist to platelets not bound to a P2Y12 antagonist induces the platelets to produce microparticles, and the number and, optionally, the size, of the microparticles is measured.

III. EQELS Techniques

Electrophoretic quasi-elastic light scattering (EQELS) is a dynamic light scattering technique in which an electric field is imposed on the sample for characterizing particles in a medium, which utilizes electrophoresis, in which particles are characterized by their movement in an applied electric field. The particle can then be characterized with respect to size and particle surface charge. This technique may be used for the characterization of platelets in media containing the same and may employ a superimposed electric field to freely allow these platelets to electrophorese.

The electrophoretic mobility of the platelets in the solution depends on both the size of the platelets, the total charge on the platelets, and the strength of the superimposed field. Electrophoretic mobility as used herein refers to motion induced in suspended charged particles that result from the effect of a superimposed electric field and is balanced by the viscous drag of the solvent on the particle. The electrophoretic mobility can be used to calculate size, weight and distributions thereof. It should be understood that the size of a particle is generally equivalent to its diffusion coefficient.

Without wishing to be bound by any particular theory, when the particle is large compared to the Debye Huckle length, the surface charge generally governs the movement of the particle. The Debye Huckle length is defined by the layer of solvent counter ions organized over charged surface of the suspended particle and the thickness of the layer depends on the magnitude of the particle surface charge and the ionic strength of the suspending solution.

FIG. 10 is a schematic illustration showing the effect platelets on the cations in the solution that surrounds the particle, as described by Debye Huckle theory. The yellow circle represents a platelet. Platelets in the resting state have a negative surface charge.

For a short distance out from the platelets, where the electrical potential is high, the positive ions in solution orient themselves around the cells. That layer is called the Stern layer. As one moves out farther the electric field, a decrease in strength as shown in the graph. In this area, the ordering of oppositely charged ions is not as distinct, and some negatively charged solution ions can enter this area. This layer is called the diffuse layer. The thickness of the diffuse layer is called the Debye length.

EQELS works by making the cell move in an imposed electric field. Because the electric field at the far reaches of the diffuse plane is not intense enough to drag the entire cloud of ions with it, some are left behind. The distance from the cell surface where this occurs is called the "shear plane". The potential at that point is called the "zeta potential."

In an imposed electric field, charged particles will move in one direction or another, depending on the charge on the particles. Un-activated platelets have an overall negative charge, and activated platelets (activated by a P2Y12 agonist such as ADP) have an overall positive charge. The movement of the platelets indicates whether a pre-administered P2Y12 antagonist is functioning to protect the platelets from activation (i.e., the direction of movement indicates that the patient can properly metabolize a P2Y12 prodrug, and the patient's platelets are capable of binding to the active P2Y12 antagonist).

Systems suitable for analyzing the electrophoretic mobility distribution of platelets in a sample medium are described, for example, in PCT WO 2005008241, the contents of which are hereby incorporated by reference in their entirety.

The systems include an Electrophoretic Quasi-elastic Light Scattering (EQELS) spectrometer comprising an EQELS controller configured to measure the mobilities of platelets on the basis of their charge, and to generate an EQELS spectrum for the platelets in the sample medium. An EQELS analyzer is in communication with the EQELS spectrometer. The EQELS analyzer is configured to determine the electrophoretic mobility distribution of the separated platelets from the EQELS spectrum. The system can be used to carry out various steps described herein. In some embodiments, the EQELS spectrometer is further configured to generate a photon correlation spectroscopy (PCS) spectrum of the sample medium. For example, the electric field in the EQELS spectrometer may be deactivated for PCS spectroscopy. The EQELS analyzer is further configured to determine a molecular size distribution based on the PCS spectrum of the sample medium.

According to further embodiments of the present invention, methods of detecting electrophoretic mobility and/or size distribution characterization of platelets in a sample medium include impinging energy on the sample medium to generate an energy interaction output. Using EQELS, one can determine an electrophoretic mobility distribution of the particles. With PCS (DLS), there is a diffusion coefficient distribution, and, accordingly, one can determine a size distribution of the platelets in the sample medium. Both determinations can be determined based on the energy interaction output.

For example, the presence of a positive or negative surface charge on the platelets, following administration of a P2Y12 agonist such as ADP to platelets pre-exposed to a putative P2Y12 antagonist, can be determined based on the electrophoretic mobility distribution and/or size distribution of the platelets. Impinging energy can include impinging light energy on the sample medium. A size distribution of platelets can be determined using photon correlation spectroscopy (PCS) or electrophoretic quasi-elastic light scattering (EQELS).

The sample medium can include plasma or components thereof and/or a dilute buffer salt solution. The energy interaction output can be produced under electrophoretic or non electrophoretic (PCS) conditions.

The sample medium can be provided by adding an amount of a P2Y12 agonist, such as ADP, to a plasma sample derived from a subject. A presence or absence of binding of the P2Y12 agonist to the platelets in the plasma sample can be determined based on the electrophoretic mobility (EQELS) and/or size distribution of the platelets (ISADE) or platelet MPs generated by platelet activation (ISADE) in the sample medium.

That is, activated platelets are larger than un-activated platelets, so the activation can be measured by particle size. However, in one aspect of this embodiment, the activation is measured by the concomitant change in surface charge on the platelets.

A determination of whether or not the patent will benefit from the particular P2Y12 antagonist therapy can be made based on the presence or absence of platelets with a positive charge in the plasma sample derived from the subject. The presence of positive charge is indicative of the activation of the platelets, which is indicative of failure of the P2Y12 antagonist to protect the platelets from such activation. The absence of a positive charge is indicative of the inactivation of the platelets, which is indicative of the success of the P2Y12 antagonist to protect the platelets from such activation. In those embodiments where the P2Y12 antagonist is a prodrug, the subject can be administered a putative therapeutic agent sufficiently ahead of time such that the platelets will be protected if the patient is able to metabolize the prodrug, and if the patient's platelets are capable of binding to the P2Y12 antagonist.

An electrophoretic mobility and/or size distribution of platelets can optionally be determined from a first sample taken from the subject before administering the therapeutic agent and/or procedure and from a second sample taken from the subject after administering the therapeutic agent. However, since the charge of an unactivated platelet is known, it is not necessary to determine the electrophoretic mobility of the sample before exposure to the P2Y12 agonist. The effectiveness of the therapeutic agent can be assessed based on the electrophoretic mobility of the platelets from the first and second samples, or, preferably, solely from the second sample. The key point is that the differences in the particles electrostatic finger print can be measured. One fingerprint will move at one rate and a different fingerprint will move at another rate.

Other Techniques For Measuring Particle Movement Based on Surface Charge

In addition to Electrophoretic Quasi-elastic Light Scattering (EQELS) spectroscopy, it should be understood that other electrophoretic interaction spectral techniques (i.e., techniques in which a biological particle in an electrophoretic field interacts with an energetic medium to generate a spectrum) and/or non-electrophoretic techniques can be used. Spectroscopy techniques that do not employ an electrophoretic field include photon correlation spectroscopy (PCS).

Moreover, although embodiments of the present invention are described with respect to an excitation light beam, other energetic media can be used, including electromagnetic energy, or other suitable energy media. For example, electromagnetic energy can be employed from any suitable spectral range, such as visible light, infrared, ultraviolet, and/or x-ray ranges. For example, actinic radiation having a wavelength from about 200 nm to about 700 nm can be used as an energetic medium for interaction with platelets in an electrophoretic field. Visible light radiation can be used in light-scattering techniques, including elastic light scattering and quasi-elastic light scattering. Thus, any suitable energy source and corresponding energy medium can be used.

In some embodiments, characteristics of a spectrum from a sample are used to determine whether or not a patient will benefit from a particular P2Y12 antagonist therapy. Set out below is a discussion of the various spectral techniques. Dynamic light scattering (DLS) involves particle-mediated scattering of light that is impinged on an inhomogeneous (particle-containing) medium and the measurement of the temporal autocorrelation function for a scattering vector at a specific scattering angle.

From a scattering intensity and the autocorrelation function, one can determine particle size (hydrodynamic radii), shape factors and/or other characteristics of the particles in the particle-containing medium. Dynamic light scattering is also referred to as photon correlation spectroscopy (PCS). DLS can be conducted by turning off the electric field off, but the advantages of being able to obtain resolution between resting and activated platelets will be lost.

Thus, embodiments of the present invention are carried out with dynamic light scattering (DLS) techniques, which may also be referred to as photon correlation spectroscopy (PCS). Other energy interaction techniques may also be used. The term "quasi-elastic" may be used to describe interactions between photons and particles in the spectroscopy techniques described herein because such interactions are not perfectly elastic. That is, when the photon hits the scattering particle, it loses a relatively small amount of energy.

The incident light used in the techniques described herein may be generally coherent. Coherent light is, in general, defined as light, or photons, that all have essentially identical wavelengths that are "in phase." Coherent light may be obtained from lasers. Therefore, incident light is unshifted coherent light used to illuminate the scattering particles. Incoherent light may also be used.

As used herein, scattered light may refer to inelastic (including quasi-elastic) or elastic scattering from a target. Photons generally have wave properties that result from an orthogonal arrangement of an electric field and a magnetic field. In light scattering, as the light encounters the particle, the electric field causes the electrons in the particle to move up and down. The oscillatory movement of the electron causes a secondary field to be established. This field forms the scattered light. Scattered light can include light that results from the oscillatory motion of the electron in the scattering particle that is induced by incident light.

When the photon in the incident light interacts with the scattering particle, the photon loses a small amount of energy, which results in a slight decrease in the frequency of the incident light. This "phase shift" (also referred to as the Doppler shift) in the scattered light compared to the incident light is the basis for the measurement. The shift in the frequency is detected by mixing the un-scattered light with the scattered light (heterodyning) on the photo-detector. "Beats" result, and the magnitude of the frequency of the beats is generally proportional to the mobility of the scattering particle. In the case of EQELS, the magnitude of the frequency of the beats is proportional to the electrophoretic mobility of the particle. In contrast, in PCS or QELS, the motion of the particle may be proportional to its diffusion coefficient.

Calculation of Electrophoretic Mobility

The autocorrelation function is a statistical mechanics method for the correlation of the relative positions of a large number of particles (ensemble) and, for example, can have the general formula:

$$g^{(2)}(\tau) = \langle I(t)I(t+\tau) \rangle \quad \text{Eq. 1}$$

where $\tau$ is the time increment, I is scattered intensity, and t is time. In some embodiments, the time dependence of the autocorrelation function is used to determine the movement over time of an ensemble of scattering particles. The calculation of the electrophoretic mobility may be performed as follows. In some embodiments, the experimental results can be presented in several different formats of quantitative indicia including: (1) the frequency shift, (2) the zeta potential and/or (3) the electrophoretic mobility. The data can also be presented in a form that can include: (1) the diffusion coefficient, (2) the characteristic dimension and/or (3) the particle size. The latter two quantities may be calculated from the diffusion coefficient for each platelet. The diffusion coefficient for each platelet can be determined as follows. If each platelet in the mobility spectra is homogeneous with respect to particle size (as it should be by virtue of the electrophoretic technique) then the morphology or the line shape of each band in the spectra should be Lorentzian. A Lorentzian line shape is defined as:

$$I_{(S,v)} = \frac{\langle N \rangle S^2 D}{\pi (4\pi^2 v^2 + (S^2 D)^2)} \quad \text{Eq. 2}$$

The ½ width at ½ height of the individual bands, representing a specific platelet population, is S2D, so by plotting the V, width of each and versus sin 2(⊖), D can be determined. It will be appreciated that an electrophoretic mobility distribution can thus be determined and/or displayed directly from a calculated and/or displayed electrophoretic mobility distribution, or indirectly from other quantitative indicia as described above.

An exemplary EQELS spectrometer 10 is disclosed in PCT/US2004/021715, the contents of which are hereby incorporated by reference in its entirety. The spectrometer includes a laser that impinges a beam of light onto a sample. The sample is positioned between two electrodes that provide an electric field to the sample. Charged platelets in the sample are induced to move due to the application of the electric field.

Movement of the particles in the sample is detected by quasi-elastic scattering from the generally coherent light provided by the laser. Some of the incident photons can encounter moving particles in the sample. When this encounter occurs, a small amount of energy from the photon is given up, and consequently, the frequency of the scattered light is slightly reduced. This scattered light is detected by a detector.

The spectrometer is connected to a processor that includes an EQELS signal analyzer. The processor receives signals from the spectrometer, which are analyzed by the EQELS signal analyzer. For example, the scattered light detected by the detector can be analyzed to determine the magnitude of the small shift in frequency. This shift in frequency is generally proportional to the rate of movement of the particle in the sample and is detected as a Doppler shift. The signal analyzer can measure the Doppler shift through a heterodyne technique in which unshifted light is mixed with the scattered light to produce "beats". This signal is measured as an autocorrelation function that can then be Fourier transformed to yield a power spectrum for interpretation. The electrophoretic mobility is determined from the power spectrum.

A data processing system can be provided that includes a processor in communication with a spectrometer, and a memory. Various types of spectrometers may be used, such as PCS, DLS, and EQELS spectrometers. The spectrometer can include a sample modification system. The sample modification system is configured to modify the sample in the spectrometer, such as by adding a P2Y12 agonist.

In some embodiments, the spectrometer and/or the sample modification system is omitted. For example, the sample can be modified manually or a spectrum can be obtained according to embodiments of the invention without modifying the sample with the sample modification system. In some embodiments, the spectrometer is omitted and a spectrum obtained from a remote spectrometer is provided to the data processing system for analysis.

The sample modification system can modify the sample, for example, by adding a P2Y12 agonist such as ADP, adding a solvent, changing the pH of the sample medium, changing the temperature of the sample medium, changing the ionic strength of the sample medium, and the like. Sample purification can be accomplished by any of a variety of affinity (immuno- or ligand-) methods.

The processor communicates with the memory via an address/data bus. The processor can be any commercially available or custom microprocessor. The memory is representative of the overall hierarchy of memory devices containing the software and data used to implement the functionality of the data processing system. The memory can include, but is not limited to, the following types of devices: cache, ROM, PROM, EPROM, EEPROM, flash memory, SRAM, and DRAM.

The memory may include several categories of software and data used in the data processing system: the operating system; the application programs; the input/output (I/O) device drivers and the data. The data may include a database of known spectral profiles and/or spectral data from the spectrometer. The database of known spectral profiles and/or spectral data can be used to identify or characterize a sample. For example, spectra from samples where platelets were not activated can be used to determine parameters for determining whether a particular P2Y12 antagonist is effective. A spectrum falling within such parameters can then be viewed as correlating to the success of the PY12 antagonist in protecting the platelets from activation by the P2Y12 agonist.

As will be appreciated by those of skill in the art, the operating system may be any operating system suitable for use with a data processing system, such as OS/2, AIX, OS/390 or System390 from International Business Machines Corporation, Armonk, N.Y., Windows CE, Windows NT, Windows95, Windows98, Windows2000, or WindowsXP from Microsoft Corporation, Redmond, Wash., Unix or Linux or FreeBSD, Palm OS from Palm, Inc., Mac OS from Apple Computer, Lab View or proprietary operating systems.

The I/O device drivers typically include software routines accessed through the operating system by the application programs to communicate with devices such as I/O data port (s), data storage and certain components of the memory and/or the spectrometer. The application programs are illustrative of the programs that implement the various features of the data processing system and preferably include at least one application which supports operations according to embodiments of the present invention. The data represents the dynamic data used by the application programs, the operating system, the I/O device drivers, and other software programs that may reside in the memory.

As will be appreciated by those of skill in the art, various configurations can be utilized while still benefiting from the teachings of the present invention. For example, the spectral profile analysis module may also be incorporated into the operating system 1, the I/O device drivers or other such logical division of the data processing system. Thus, the present invention should not be construed as limited to the configuration described herein.

The I/O data port can be used to transfer information between the data processing system and the spectrometer or another computer system or a network (e.g., the Internet) or to other devices controlled by the processor. These components may be conventional components such as those used in many conventional data processing systems that may be configured in accordance with the present invention to operate as described herein.

It should be understood that various types of spectrometers and spectrometry techniques may be used, including electrophoretic spectrometers and/or spectrometers in which the sample is not positioned in an electric field. For example, EQELS, PCS or DLS spectrometers may be used for the spectrometer. Moreover, other techniques can be used to impinge energy to a sample and to collect an energy interaction output from the sample.

The light-scattering based techniques according to embodiments of the present invention, are based on differences in the frequency between light scattered from the moving particle and the incident light impinged on the particle. Since the very small shift in the frequency of the scattered light may not be measured directly, a heterodyne method is used in which the scattered light is mixed with the reference or unshifted light [Johnson, Jr., CS. Laser Light Scattering. Dover Press, NY, 1994]. The difference in the frequency between the shifted and unshifted light gives rise to 'beats.' The frequency of beats is related to the magnitude of the frequency shift in the scattered light which is in turn related to the mobility of the scattering particle, e.g., platelet. The electrophoretic effect is obtained by superimposing a uniform electric field (which may range from about a few volts/cm to about 30,000 volts/cm) depending on the electrophoretic method used. The field is pulsed and its polarity alternated to avoid sample polarization. The scattered intensity (Is) from a moving particle at a fixed angle (Θs) is observed as an oscillating intensity in the heterodyne methodology as a second order field autocorrelation function G2 hel(τ) Bern, B J. Dynamic Light Scattering. John Wiley & Son, NY 1976] given by the Equation:

$$G_{thet}^2(\tau) = I_L^2 + 2I_L \langle I_S \rangle \cos(K \cdot v_d \tau) e^{-DK^2 \tau} \qquad \text{Eq. 3}$$

where I is the intensity of the reference beam (local oscillator), and Is is the intensity of the scattered light, Vd is the velocity of the scattered particle, D is the diffusion coefficient and τ is the time increment. K is the scattering vector defined by:

$$K = \frac{4\pi n}{\lambda} \sin\left(\frac{\theta_s}{2}\right) \qquad \text{Eq. 4}$$

where n is the refractive index, and λ is the wavelength of the incident light. One important quantity in this expression is K·Vd, the Doppler shift of the signal resulting from the particle motion. Fourier transform of the measured autocorrelation function gives the power spectrum from which the particle electrophoretic mobilities are calculated [Ware, BR. Electrophoretic light scattering. Adv. Colloid Interface Science 4:1-44, 1974].

Temperature, ionic strength, pH, and conductivity of a sample medium may be controlled. Small changes in temperature can be detected by a change in the conductivity, which may be monitored throughout the experiment. Joule heating can be governed by regulation of the pulse duration and the frequency of the electric field. Thermal lensing may be avoided by control of the incident laser power. Snell's law correction may be made for all scattering angles. The electrokinetic properties of activated and un-activated platelets lie in the area of the Debye-Huckel equation where both surface charge and frictional forces are significant to its movement in an electric field. For example, both the electrical charge and frictional properties of the platelets may contribute to the mobility spectra [Pthica BA. The physical chemistry of cell adhesion. Exp. Cell Res. 8, 123-140, 1961].

Without wishing to be bound by any particular theory, the basis for resolution and distinction between activated and un-activated platelets using the EQELS technique is generally the difference in the electrophoretic mobility for these platelets.

Electrophoretic mobility is the movement of a charged particle species under the influence of an electric field.

In the absence of an electric field to induce electrophoretic mobility, such as is the case with DLS or PCS techniques (which may be substituted for the EQELS techniques discussed herein), the platelets may still undergo movement resulting from thermal effects. The magnitude of such movement, e.g., involving Brownian movement, convective currents and/or diffusional effects, can be determined by solvent conditions, solute concentration, and the molecular size of the scattering particle. Thus, although EQELS may be used to distinguish between the surface charge on activated and unactivated platelets, PCS or DLS can also be used to activated or un-activated platelets based on differences in the diffusion coefficients of the various species. PCS thus differs from EQELS in that PCS measures the diffusion coefficient of the platelets, whereas EQELS measures the electrophoretic mobility of the platelets.

Differences in the magnitude of movement of the diffusing species are detected from differences in the magnitude of the Doppler shift that result from the interaction of incident photons, such as can be produced by a laser or other light source, and the diffusing species. The rapidly translating or diffusing species can yield a larger Doppler shift and slower diffusing species can yield a smaller Doppler shift. The detection method otherwise corresponds to that employed for EQELS. PCS can provide an accurate method for determining translational diffusion coefficients for the analysis of platelets.

By way of illustration, the EQELS technique can be carried out using a sample cell contained in a refractive index matching vat, using toluene as the refractive matching fluid and temperature controlled within a tolerance of 0.1° C. The scattered radiation can be measured by a photo-tube positioned at a defined scattering angle. The z-averaged translational diffusion coefficient may then be obtained from the intensity-normalized photon count autocorrelation function as the slope of the decay constant $-T$ vs. $\sin(\ominus s/2)$ where $T=KD$ and $K$ is the scattering vector. The molecular size can be expressed as a hydrodynamic diameter and calculated from D defined by Einstein's equation. Based on exponential sampling techniques, the molecular size distributions (e.g., variation in the size of activated or un-activated platelets) can be derived from the PCS autocorrelation function.

The size of the platelets can be attributed, at least in part, to activation of the platelets by the P2Y12 agonist. The particle size can be determined by looking at the diffusion coefficients, using DLS, or by using the ISADE apparatus described herein, but not using EQELS, which is used to determine the electrophoretic mobility of the particles.

The present invention therefore provides a rapid assay method for identifying patients who will or will not likely benefit from a particular P2Y12 antagonist therapy.

The rapid assay methods of the invention include, without limitation, methods utilizing dynamic light scattering methods including EQELS (Electrophoretic Quasi Elastic Light Scattering, PCS (Photon Correlation Spectroscopy) and the like, or other methods for detecting the electrophoretic mobility of platelets, by impinging energy on a medium containing the platelets, to generate an energy interaction spectrum, and determining the electrophoretic mobility and/or size distribution of the platelets following exposure to a P2Y12 agonist.

The energy interaction spectrum generally can be of any suitable type, including energy scattering spectra, energy absorbance spectra, energy transmittance spectra, or any other spectrum indicative of the energy/particle interaction involving such species and/or agents. The energy interaction may be conducted under electrophoretic or non-electrophoretic conditions, and the energy source can be of any suitable type effective to generate the desired interaction spectrum, including, without limitation, electromagnetic energy, acoustic energy, ultrasonic energy, or any other suitable energetic medium.

In the case of electromagnetic energy, the energy can be of appropriate spectral regime, such as visible light, infrared, ultraviolet, and x-ray spectral regimes.

In specific embodiments, actinic radiation is employed as the energetic medium for interaction with the platelets in the sample, and such radiation can for example have a wavelength in a range of from about 200 nm to about 700 nm.

Various embodiments of the invention employ visible light radiation, such as light-scattering techniques including elastic light scattering and quasi-elastic light scattering. It will therefore be recognized that any suitable energy detection source and corresponding energy medium can be employed in the broad practice of the invention. In various preferred embodiments, a visible light laser is utilized as the energy detection source, for conducting dynamic light scattering methods such as EQELS (Electrophoretic Quasi Elastic Light Scattering), PCS (Photon Correlation Spectroscopy) and the like.

The determination of whether the platelets have a positive or negative surface charge, from the energy interaction spectra, may be made in a suitable manner, using any appropriate software, systems, analytical techniques, algorithms, etc. for such determination.

Treatment of a patient at risk of thrombosis within an artery or vein may include administering a therapeutically effective amount of a P2Y12 antagonist identified using this screening assay as having a effect to prevent activation and aggregation of platelets.

The prevention of platelet activation prevents blockage of the blood vessel. The scattered light output processing steps can be conducted in a very rapid manner, such as less than 5 minutes, less than 1 minute, or even less. The sample can be held in a chamber, which may, for example, be the electrophoretic cell of an EQELS apparatus.

The medium containing the platelets can for example include a buffered dilute salt solution, patient plasma, purified (e.g., chromatographically purified) plasma, or other physiological fluid or reagent solution. In one embodiment, a blood sample is centrifuged to produce platelet-rich plasma and platelet-poor plasma.

The impingement of the energy on the patient sample and responsive generation of an energy interaction output includes dynamic light scattering methods such as EQELS (Electophoretic Quasi Elastic Light Scattering, PCS (Photon Correlation Spectroscopy) and the like.

IV. Use of EQELS Techniques to Identify Patients Who Benefit from Therapy

As discussed above, the assay involves obtaining a blood sample, which may be purified, from a patient. The sample medium can be purified, for example, using chromatographic purification and/or centrifugation. Where the P2Y12 antagonist that is administered is a prodrug that must first be metabolized, the patient is either given a loading dosage of the agent, or is provided the agent in a sufficient amount, and for a sufficient period of time, to provide a satisfactory level of the active metabolite should the patient be able to benefit from the treatment. If the P2Y12 antagonist is the active agent, rather than a prodrug, then the agent can be administered directly to the blood sample, and incubated for a sufficient period of time to permit the agent to bind to P2Y12 receptors on the surface of the platelets.

Optionally, the sample can be subjected to dynamic light scattering spectroscopy, using EQELS or PCS, as described herein, before a P2Y12 agonist such as ADP is added to the sample, to provide a baseline reading. However, since the surface charge of unactivated platelets (whether or not bound to a P2Y12 antagonist) is known, this step is optional.

The sample is then incubated with ADP or other suitable P2Y12 agonist, and then dynamic light scattering spectroscopy is carried out using one or more of EQELS or PCS.

Where the electrophoretic mobility of the platelets is indicative of the platelets retaining their negative (surface) charge (or resting state), the result is indicative of the particular P2Y12 antagonist being a successful treatment for the patient.

Where the electrophoretic mobility of the platelets is indicative of the platelets losing their negative charge (i.e., becoming positively charged), the result is indicative of the particular P2Y12 antagonist not being a successful treatment for the patient.

In the case of an unsuccessful result, it may be possible to administer different dosages of the agent, and re-test the patient's sample, to determine whether the patient might benefit from a higher dosage.

V. Methods for Performing High Throughput Bioassays

Any and all of these assays can be optimized for high throughput screening using suitable robotics. Liquid handlers can transfer samples to a multi-tube or multi-well plate, and a "memory map" can be used to correlate the samples to their location on the plate.

Information on each sample can then be stored, and used to provide information about drug candidates, patient diagnoses, and proposed patient treatment options. Robotics systems are known in the art, and can be used to move samples taken from individual patients to known positions in a multi-tube or multi-well plate. Once information on the sample is obtained using the focused light scattering techniques or EQELS technique described herein, the information can be correlated to the individual patient via the stored information correlating the location of the tube and the patient identification. Liquid handlers can take portions of the sample and evaluate a plurality (i.e., at least two) of different screening assays, for example, by incubating portions of the sample with different microparticles, bound to different active agents. Automated processes can use known robotics to pull and place samples (like high throughput screening) with use of a "memory map". A user can then pick desired screens to be run and the robotic apparatus will implement desired processes.

In another aspect of the embodiments described herein, the methods can be automated using robotics to pull and place samples (analogous to conventional high throughput screening methods), optionally in conjunction with a "memory map". A user can then pick desired screens to be performed, and the robotic apparatus can implement the desired processes. In this embodiment, a laboratory can be set up to automatically screen numerous samples. In a preferred embodiment, the personalized medicine processes described herein are automated, to provide relatively inexpensive, and relatively fast, high throughput screening methods to identify preferred therapies for patients suffering from disease.

VI. Theranostic Methods

According to further embodiments of the present invention, methods of identifying a subject as potentially benefiting from a putative P2Y12 antagonist, and treating the patient with the P2Y12 antagonist if the patient is identified as potentially benefiting from the antagonist, are also disclosed.

According to further embodiments of the present invention, methods of treating a subject with a disease state or physiological condition associated with blood clotting and the concomitant clogging of arteries include: administering to the subject a therapeutic agent identified as being effective for protecting the patient's platelets from activation by P2Y12 agonists such as ADP; after administering the therapeutic agent, obtaining from the subject a physiological sample of a type which includes the patient's platelets; adding to the physiological sample an amount of ADP or other suitable P2Y12 agonist; performing dynamic light scattering spectroscopy on the sample medium to determine an electrophoretic mobility distribution and/or size distribution of the platelets attributable to activation of the platelets by the P2Y12 agonist, and determining the efficacy or non-efficacy of the therapeutic agent based on the electrophoretic mobility distribution and/or size distribution of the platelets.

As discussed above, the screening methods are applicable to identification of other suitable anti-thrombotic agents (in this case platelet inhibitors), binding to other receptors than P2Y12. Other anti-thrombotic agents include antagonists (inhibitors) of receptors such as Protease-Activated Receptor 1 (PAR1), Protease-Activated Receptor 4 (PAR4), GPIV, Thromboxane receptor (TP receptor, including TP-alpha and TP-beta), vWF antagonists, and Glycoprotein Ib (platelet), alpha polypeptide (GP1BA) also known as CD42b (Cluster of Differentiation 42b), GPIb, antagonists, and Glycoprotein IIb/IIIa (GPIIb/IIIa) antagonists. Terutroban is a representative TP inhibitor.

Representative PAR1 inhibitors include SCH 530348, SCH 205831, SCH 602539, and E5555.

Representative GP1b inhibitors include vWF, ARC 1779, ALX 0081 and AJW 200. Representative GPIIb/IIIa inhibitors include Abciximab, Eptifibatide, and Tirofiban.

In another embodiment of the invention, these inhibitors are also screened using methods analogous to those described above with respect to P2Y12.

Whereas the embodiments related to P2Y12 antagonists involve incubating cells with a P2Y12 antagonist, and exposing the incubated cells to a P2Y12 agonist, these embodiments involve incubating the cells with a PAR1, PAR4, GPIV, TP receptor (including TP-alpha and TP-beta), GPIb, GP1BA, or GPIIb/IIIa antagonist. The incubated cells are then exposed to the corresponding agonists.

For PAR1, thrombin is a suitable agonist. For GP-1b, von Willebrand Factor (vWF) is a suitable agonist. For TP receptors, thromboxane A2 (TXA2) is a suitable agonist. The peptide AYPGKF is a representative PAR-4 agonist, which is known to stimulate thromboxane production by human platelets (see, for example, Henrickson and Hanks, Arteriosclerosis, Thrombosis, and Vascular Biology. 2002; 22:861). Fibrinogen is a ligand for the GPIIb/IIIa receptor. EP80317 is a representative GPIV agonist.

VII. Kits Useful for Rapid Analysis of Electrophoretic Mobility of Platelets

According to further embodiments, an assay kit for the rapid determination of the ability of a patient to benefit from a particular P2Y12 antagonist is provided. The kit includes a means for obtaining an amount of a physiological sample from a subject of a type in which the platelets are present in a normal subject; an amount of P2Y12 agonist for addition to the physiological sample, to provide a sample medium for dynamic light scattering methods such as EQELS (Electophoretic Quasi Elastic Light Scattering, PCS (Photon Correlation Spectroscopy) and the like which provide an analysis of electrophoretic mobility and/or size distribution of platelets and platelet microparticles (ISADE) therein attributable to activation of the platelets by the P2Y12 agonist, wherein the ability of a P2Y12 antagonist to protect the platelets from activation is determinable. The assay kit can also include written instructions for conducting the rapid determination.

The present invention will be better understood with reference to the following non-limiting example.

EXAMPLE 1

Using EQELS to Measure the Electrophoretic Mobility of Activated Platelets

Platelet activation and aggregation underlies the basic "acute event" in arterial thrombosis, including strokes, peripheral artery disease and coronary artery disease (heart attacks). Current drug therapy involves using irreversible P2Y12 antagonists to bind to P2Y12 receptors on the surface of the platelets, so that the platelets to not bind to P2Y12 agonists such as adenosine diphosphate (ADP). Platelets not bound to one of these antagonists, whether reversibly or irreversibly, will bind to ADP.

The drug clopidogrel (Plavix®) is a P2Y12 antagonist that binds to the P2Y12 receptor on the platelet surface, and is marketed as an anti-thrombotic agent. Plavix itself is a pro-drug, which is metabolized in the liver to form an active agent. When the active agent is bound to P2Y12, ADP cannot bind, and platelet activation is inhibited.

In responding patients, this drug is life-saving. Unfortunately, roughly 30% of patients do not respond, and the majority of these are patients who cannot produce the active metabolite of Plavix®.

Figure 14:
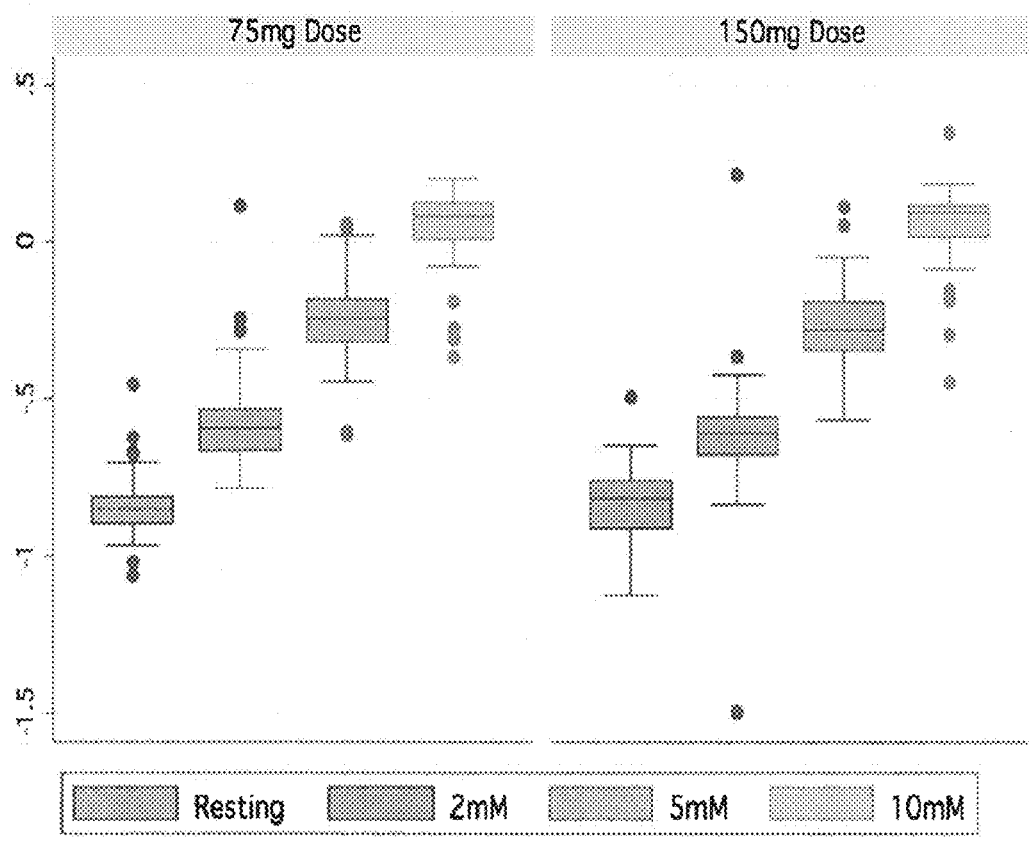
FIG. 14 is a chart showing results from an EQELS assay of the electrophoretic mobility of platelets. Blue represents the electophoretic mobility for resting human platelets (i.e. unactivated). Pink, green and yellow show the results for platelets (derived from patients with a genotype that does not activate Plavix) contacted with 2, 5, and 10 mM of ADP, a platelet activator, following administration of 75 or 150 mg of Plavix (a drug that inhibits platelet activation).

In order to provide a rapid assay to distinguish between patients who do and do not benefit from Plavix®, a series of patients (50 total patients) were identified who had have a genotype that does not activate Plavix®. These patients were exposed to both doses of Plavix (75 and 150 mg) in an attempt to activate Plavix, and thus protect the platelets from aggregation. Platelets were obtained from these patients, and the platelets were then exposed to 0, 2 mM, 5 mM, or 10 mM of adenosine diphosphate (ADP), which activates those platelets not protected by the metabolite of Plavix. The data from the EQELS analysis of these platelets, compared to a control of resting platelets, is shown in FIG. 14. The electrophoretic mobility of the platelets was measured. Resting platelets are shown in blue bars, and the bars shown pink, green and yellow show the results for platelets exposed to 2 mM, 5 mM, and 10 mM of ADP, respectively. The electophoretic mobility for resting (i.e. unactivated) human platelets should be the same as that of platelets exposed to ADP, if the platelets were previously exposed to (and are capable of binding to) the active metabolite of Plavix®. However, as the platelets in this study were obtained from patients who have a genotype that does not activate Plavix®, they all activate, indicating that patients with this genotype will not benefit from Plavix® treatment.

Thus, a rapid assay for identifying patients who will benefit from anti-platelet aggregation therapy is provided. Those patients who would benefit from Plavix® have platelets that, following dosing with Plavix® for a sufficient period of time to expose the platelets to the active metabolite, would have the same electrophoretic mobility as resting platelets, even after the platelets are exposed to ADP.

Accordingly, although the invention has been described herein with reference to various illustrative aspects, features and embodiments, it will be recognized that the invention is not thus limited, but rather extends to and encompasses other variations, modifications and alternative embodiments, such as will suggest themselves to those of ordinary skill in the art, based on the disclosure herein. The claims hereafter set forth therefore are intended to be broadly construed and interpreted as including all such variations, modifications and alternative embodiments within their spirit and scope.

The invention claimed is:

1. A method for determining whether a patient will benefit from administration of a P2Y12 antagonist prodrug, comprising:
   a) administering a dosage of a prodrug form of a P2Y12 antagonist to a patient, with sufficient lead time to develop an effective plasma concentration of the active metabolite, which is a P2Y12 antagonist, sufficient to bind to the platelets in the patient's blood, or a sufficient portion thereof, and thus provide a protective benefit against blood clotting resulting from platelet activation by a P2Y12 agonist, should the patient be able to metabolize the prodrug and should the patient have platelets that bind to the active metabolite,
   b) obtaining a blood sample from the patient, which blood sample comprises platelets,
   c) passing the blood sample, or a portion thereof, through a single particle optical sizing (SPOS) device to count the number of microparticles in the sample, wherein the microparticle have a diameter of around 0.1 to 0.6 microns, and the SPOS device is capable of measuring microparticles in this size range, and counting the number of such particles,
   d) incubating the sample with a P2Y12 agonist for a sufficient period of time to cause the platelets in the sample to eject microparticles in the absence of a protective benefit resulting from the administration of the prodrug, and
   e) passing the blood sample, or a portion thereof, through a single particle optical sizing (SPOS) device to count the number of microparticles in the sample, wherein an increase in the number of microparticles is indicative of the patient not receiving a protective benefit from the prodrug, as a result of the platelets not being protected from activation by the P2Y12 agonist, and wherein the lack of any significant increase in the number of microparticles is indicative of the patient receiving a protective benefit from the prodrug, as a result of the platelets being protected from activation by the P2Y12 agonist.

2. The method of claim 1, wherein the P2Y12 agonist is ADP.

3. The method of claim 1, wherein the prodrug is clopidogrel bisulfate.

4. The method of claim 1, wherein the prodrug is Prasugrel, Cangrelor, Ticlid, Parasurgrel, Elinogrel, Ticangrelor, BX667, and PRT 060128.

5. The method of claim 1, further comprising administering the prodrug to the patient if the results are indicative of the patient receiving a protective benefit from the prodrug, as a result of the platelets being protected from activation by the P2Y12 agonist.

6. The method of claim 1, wherein, if the results are indicative of the patient not receiving a protective benefit from the prodrug, as a result of the platelets not being protected from activation by the P2Y12 agonist, the patient is administered a different dosage of the metabolite, and the assay is repeated.

7. A method for determining whether a patient will benefit from administration of a P2Y12 antagonist prodrug, comprising:
   a) administering a dosage of a prodrug form of a P2Y12 antagonist to a patient, with sufficient lead time to develop an effective plasma concentration of the active metabolite, which is a P2Y12 antagonist, sufficient to bind to the platelets in the patient's blood, or a sufficient portion thereof, and thus provide a protective benefit against blood clotting resulting from platelet activation by a P2Y12 agonist, should the patient be able to metabolize the prodrug and should the patient have platelets that bind to the active metabolite,
   b) obtaining a blood sample from the patient, which blood sample comprises platelets,
   c) incubating the sample with a P2Y12 agonist for a sufficient period of time to cause the P2Y12 receptors on the surface of the platelets, or a sufficient quantity thereof, to bind to the P2Y12 agonist, if the administered prodrug does not provide a protective benefit, and
   d) determining the electrophoretic mobility of the platelets in the sample, wherein an electrophoretic mobility of the platelets in the sample that correlates to the surface charge of the platelets having a positive charge is indicative of the patient not receiving a protective benefit from the prodrug, as a result of the platelets not being protected from activation by the P2Y12 agonist, and wherein an electrophoretic mobility of the platelets in the sample that correlates to the surface charge of the platelets having a negative charge is indicative of the patient receiving a protective benefit from the prodrug, as a result of the platelets being protected from activation by the P2Y12 agonist.

8. The method of claim 7, wherein the P2Y12 agonist is ADP.

9. The method of claim 7, wherein the prodrug is clopidogrel bisulfate.

10. The method of claim 7, wherein the prodrug is Prasugrel.

11. The method of claim 7, wherein, if the results are indicative of the patient not receiving a protective benefit from the prodrug, as a result of the platelets not being protected from activation by the P2Y12 agonist, the patient is administered a different dosage of the metabolite, and the assay is repeated.

12. The method of claim 7, further comprising administering the prodrug to the patient if the results are indicative of the patient receiving a protective benefit from the prodrug, as a result of the platelets being protected from activation by the P2Y12 agonist.

13. A method for determining whether a patient will benefit from administration of a P2Y12 antagonist prodrug, comprising:
  a) administering a dosage of a prodrug form of a P2Y12 antagonist to a patient, with sufficient lead time to develop an effective plasma concentration of the active metabolite, which is a P2Y12 antagonist, sufficient to bind to the platelets in the patient's blood, or a sufficient portion thereof, and thus provide a protective benefit against blood clotting resulting from platelet activation by a P2Y12 agonist, should the patient be able to metabolize the prodrug and should the patient have platelets that bind to the active metabolite,
  b) obtaining a blood sample from the patient, which blood sample comprises platelets,
  c) incubating the sample with a P2Y12 agonist for a sufficient period of time to cause the platelets in the sample to clump, and thus increase in size, in the absence of a protective benefit resulting from the administration of the prodrug, and
  d) passing the blood sample, or a portion thereof, through a single particle optical sizing (SPOS) device to measure the size of the platelets in the sample, and determining, based on the size of the platelets, whether or not the platelets have been activated by the P2Y12 agonist, wherein an increase in the platelet size from the size of resting platelets is indicative of the patient not receiving a protective benefit from the prodrug, as a result of the platelets not being protected from activation by the P2Y12 agonist, and wherein the lack of any significant increase in the size of the platelets is indicative of the patient receiving a protective benefit from the prodrug, as a result of the platelets being protected from activation by the P2Y12 agonist.

14. The method of claim 13, wherein the P2Y12 agonist is ADP.

15. The method of claim 13, wherein the prodrug is clopidogrel bisulfate.

16. The method of claim 13, wherein the prodrug is selected from the group consisting of Prasugrel, Cangrelor, Ticlid, Parasurgrel, Elinogrel, Ticangrelor, BX667, and PRT 060128.

17. The method of claim 13, further comprising administering the prodrug to the patient if the results are indicative of the patient receiving a protective benefit from the prodrug, as a result of the platelets being protected from activation by the P2Y12 agonist.

18. The method of claim 13, wherein, if the results are indicative of the patient not receiving a protective benefit from the prodrug, as a result of the platelets not being protected from activation by the P2Y12 agonist, the patient is administered a different dosage of the metabolite, and the assay is repeated.

19. A method for determining whether a patient will benefit from administration of a PAR1, PAR4, GPIV, TP, vWF, GPIb, GP1Ba, or GPIIb/IIIa antagonists, comprising
  a) administering a dosage of a PAR1, PAR4, GPIV, TP, vWF, GPIb, GP1Ba, or GPIIb/IIIa antagonist, or prodrug thereof, to a patient, with sufficient lead time to develop an effective plasma concentration of the drug or active metabolite, as appropriate, sufficient to bind to the platelets in the patient's blood, or a sufficient portion thereof, and thus provide a protective benefit against blood clotting resulting from platelet activation, adhesion and/or platelet aggregation by a PAR1, PAR4, GPIV, TP, vWF, GPIb, GP1Ba, or GPIIb/IIIa agonist, should the patient be able to metabolize the prodrug, where the antagonist is administered in the form of a prodrug, and should the patient have platelets that bind to the drug or to the active metabolite, where the antagonist is administered in the form of the active metabolite,
  b) obtaining a blood sample from the patient, which blood sample comprises platelets,
  c) passing the blood sample, or a portion thereof, through a single particle optical sizing (SPOS) device to count the number of microparticles in the sample, wherein the microparticle have a diameter of around 0.1 to 0.6 microns, and the SPOS device is capable of measuring microparticles in this size range, and counting the number of such particles,
  d) incubating the sample with a PAR1, PAR4, GPIV, TP, vWF, GPIb, GP1Ba, or GPIIb/IIIa agonist, respectively, for a sufficient period of time to cause the platelets in the sample to eject microparticles in the absence of a protective benefit resulting from the administration of the prodrug, and
  e) passing the blood sample, or a portion thereof, through a single particle optical sizing (SPOS) device to count the number of microparticles in the sample, wherein an increase in the number of microparticles is indicative of the patient not receiving a protective benefit from the prodrug, as a result of the platelets not being protected from platelet activation, adhesion and aggregation by the PAR1, PAR4, GPIV, TP, vWF, GPIb, GP1Ba, or GPIIb/IIIa agonist, and wherein the lack of any significant increase in the number of microparticles is indicative of the patient receiving a protective benefit from the PAR1, PAR4, GPIV, TP, vWF, GPIb, GP1Ba, or GPIIb/IIIa antagonist, or prodrug form thereof, as a result of the platelets being protected from platelet activation, adhesion and aggregation by the PAR1, PAR4, GPIV, TP, vWF, GPIb, GP1Ba, or GPIIb/IIIa antagonist or prodrug form thereof.

* * * * *